(12) United States Patent  (10) Patent No.: US 7,993,389 B2
Globerman  (45) Date of Patent: Aug. 9, 2011

(54) GUIDEWIRE SYSTEM

(75) Inventor: Oren Globerman, Kfar-Shmaryahu (IL)

(73) Assignee: Existent Inc., Wilmington, DE (US)

( * ) Notice: Subject to any disclaimer, the term of this patent is extended or adjusted under 35 U.S.C. 154(b) by 1197 days.

(21) Appl. No.: 10/517,938

(22) PCT Filed: Jun. 12, 2003

(86) PCT No.: PCT/IL03/00504
§ 371 (c)(1), (2), (4) Date: Aug. 9, 2005

(87) PCT Pub. No.: WO03/105922
PCT Pub. Date: Dec. 24, 2003

(65) Prior Publication Data
US 2006/0100694 A1    May 11, 2006

Related U.S. Application Data

(60) Provisional application No. 60/387,929, filed on Jun. 13, 2002.

(51) Int. Cl.
*A61F 2/06* (2006.01)
(52) U.S. Cl. ......................................... 623/1.35
(58) Field of Classification Search .................. 623/1.11, 623/1.12, 1.35; 606/191–198
See application file for complete search history.

(56) References Cited

U.S. PATENT DOCUMENTS

| | | | |
|---|---|---|---|
| 4,932,959 A | 6/1990 | Horzewski et al. | |
| 5,045,061 A | 9/1991 | Seifert et al. | |
| 5,195,978 A | 3/1993 | Schiffer | |
| 5,254,610 A | 10/1993 | Small et al. | |
| 5,324,269 A | 6/1994 | Miraki | |
| 5,389,087 A | 2/1995 | Miraki | |
| 5,409,458 A * | 4/1995 | Khairkhahan et al. | 606/194 |
| 5,417,708 A | 5/1995 | Hall et al. | |
| 5,468,225 A | 11/1995 | Teirstein | |
| 5,472,425 A | 12/1995 | Teirstein | |
| 5,513,650 A | 5/1996 | Johansen | |
| 5,549,555 A | 8/1996 | Sohn | |
| 5,554,118 A | 9/1996 | Jang | |
| 5,569,199 A | 10/1996 | Solar | |
| 5,607,444 A | 3/1997 | Lam | |
| 5,632,762 A | 5/1997 | Myler | |
| 5,690,642 A * | 11/1997 | Osborne et al. | 623/1.11 |
| 5,769,821 A | 6/1998 | Abrahamson et al. | |

(Continued)

FOREIGN PATENT DOCUMENTS

EP    0891752    1/1999

(Continued)

OTHER PUBLICATIONS

Communication Pursuant to Article 94(3) EPC Dated Mar. 12, 2010 From the European Patent Office Re.: Application No. 03730449.0.

(Continued)

*Primary Examiner* — Kevin T Truong

(57) ABSTRACT

A tool-carrying catheter, comprising: an elongate body adapted for insertion into a blood vessel; a tool section attached to a distal side of said body; and a guide-channel adapted to carry at least a guide-wire, wherein said catheter includes an entry port into said guide-channel for said guide wire and wherein said tool includes a distal exit for said guide wire from said guide-channel, defined in a side of said tool.

30 Claims, 18 Drawing Sheets

U.S. PATENT DOCUMENTS

| | | | |
|---|---|---|---|
| 5,868,777 A | 2/1999 | Lam | |
| 6,007,517 A | 12/1999 | Anderson | |
| 6,071,285 A * | 6/2000 | Lashinski et al. | 623/1.11 |
| 6,090,133 A | 7/2000 | Richter et al. | |
| 6,096,071 A | 8/2000 | Yadav | |
| 6,165,195 A | 12/2000 | Wilson et al. | |
| 6,168,621 B1 | 1/2001 | Vrba | |
| 6,210,429 B1 | 4/2001 | Vardi et al. | |
| 6,254,628 B1 | 7/2001 | Wallace et al. | |
| 6,293,964 B1 | 9/2001 | Yadav | |
| 6,299,628 B1 | 10/2001 | Harrison et al. | |
| 6,325,826 B1 | 12/2001 | Vardi et al. | |
| 6,352,553 B1 | 3/2002 | Van Der Burg et al. | |
| 6,379,365 B1 | 4/2002 | Diaz | |
| 6,428,568 B2 * | 8/2002 | Gaudoin et al. | 623/1.11 |
| 6,780,199 B2 * | 8/2004 | Solar et al. | 623/1.11 |
| 2001/0031979 A1 | 10/2001 | Ricci | |
| 2001/0049548 A1 | 12/2001 | Vardi et al. | |
| 2002/0032457 A1 | 3/2002 | Sirhan et al. | |
| 2006/0030924 A1 * | 2/2006 | Van Der Leest et al. | 623/1.11 |

FOREIGN PATENT DOCUMENTS

| | | |
|---|---|---|
| EP | 1031328 | 8/2000 |
| EP | 1074227 | 2/2001 |
| EP | 1 212 991 | 6/2002 |
| WO | WO 97/17101 | 5/1997 |
| WO | WO 98/19634 | 5/1998 |
| WO | WO 98/36709 | 8/1998 |
| WO | WO 98/37833 | 9/1998 |
| WO | WO 98/47447 | 10/1998 |
| WO | WO 99/36002 | 7/1999 |
| WO | WO 99/62415 | 12/1999 |
| WO | WO 00/44319 | 8/2000 |
| WO | WO 00/44946 | 8/2000 |
| WO | WO 00/56227 | 9/2000 |
| WO | WO 00/56228 | 9/2000 |
| WO | WO 00/74595 | 12/2000 |
| WO | WO 01/17602 | 3/2001 |
| WO | WO 03/017872 | 3/2003 |
| WO | WO 03/105922 | 12/2003 |

OTHER PUBLICATIONS

Response Dated Sep. 8, 2010 to Communication Pursuant to Article 94(3) EPC of Mar. 12, 2010 From the European Patent Office Re.: Application No. 03730449.0.

* cited by examiner

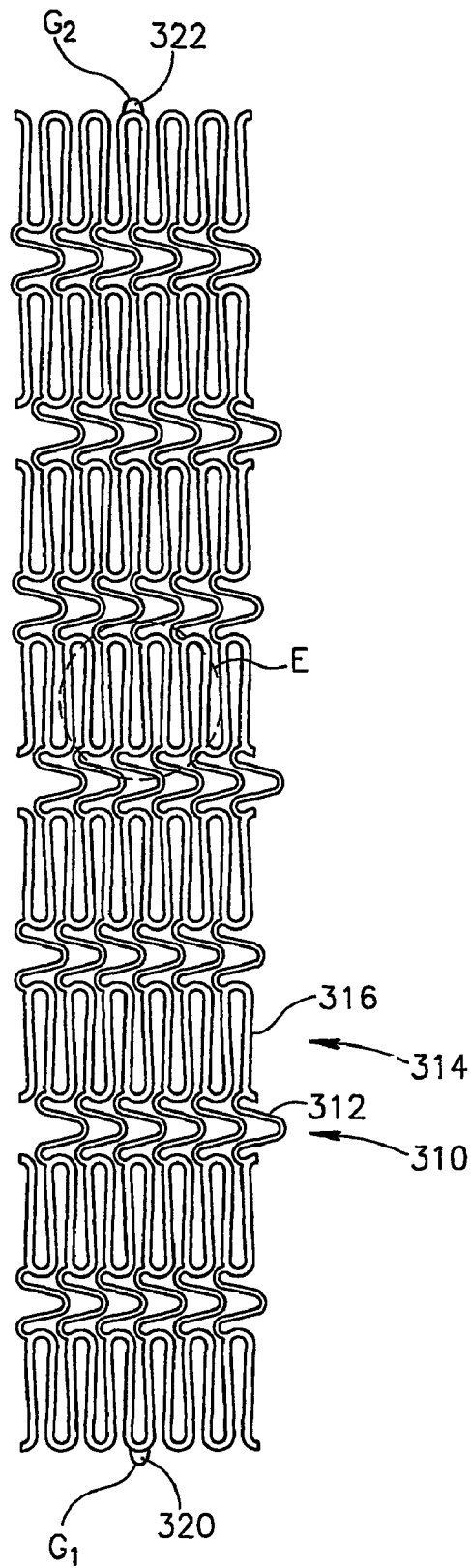
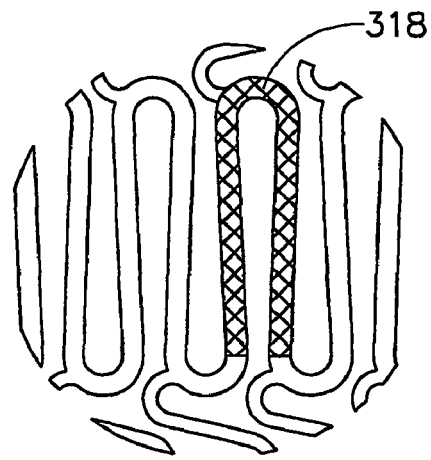
FIG.3E
FIG.3D

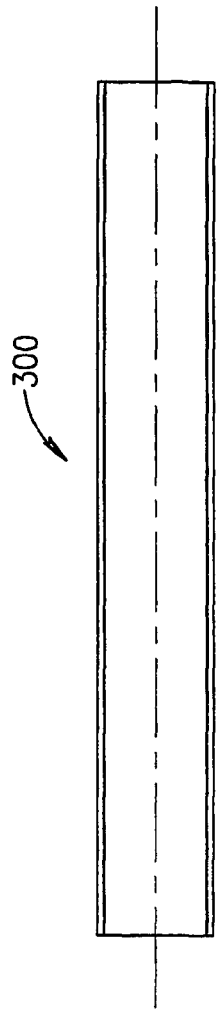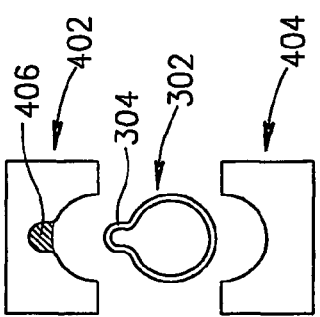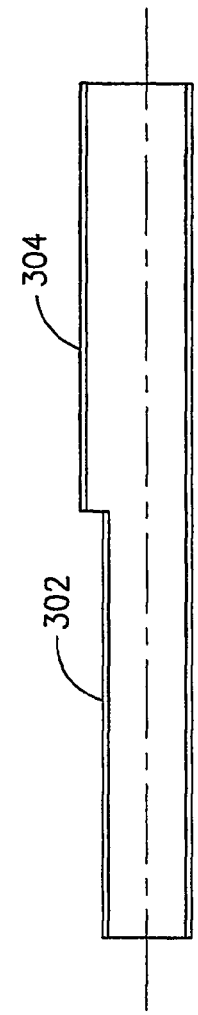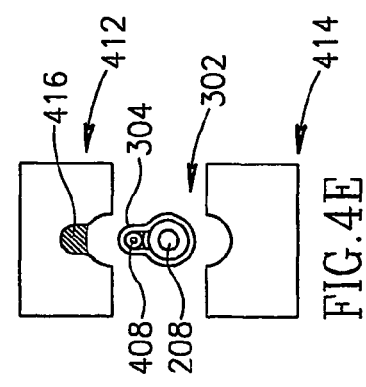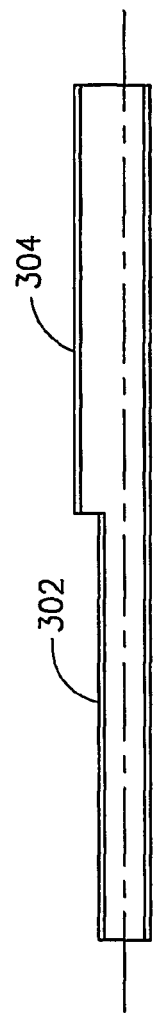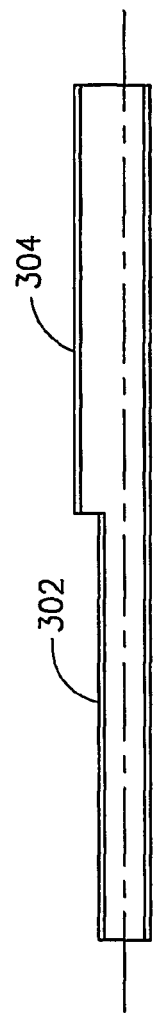

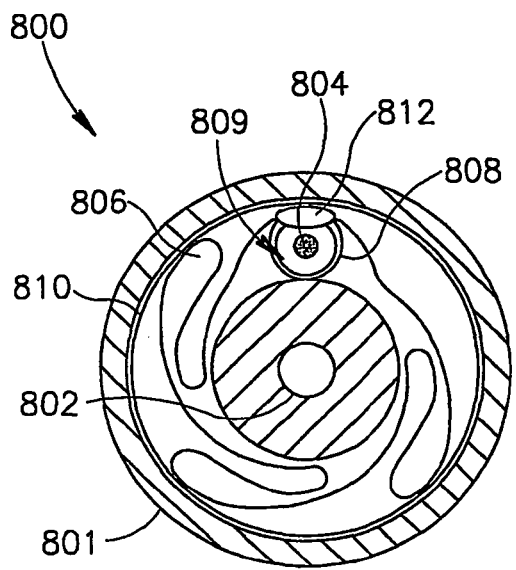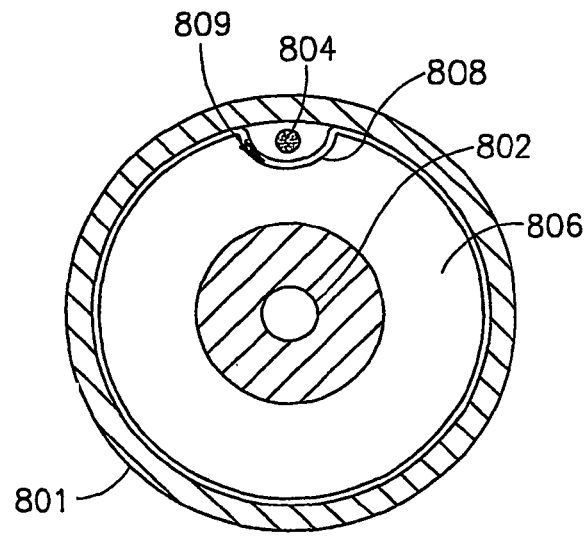
FIG.8A        FIG.8B
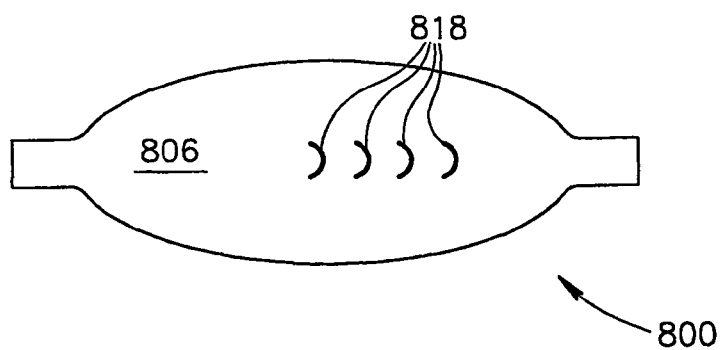
FIG.8C
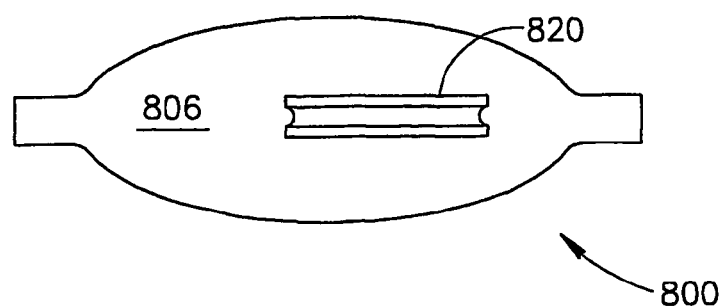
FIG.8D

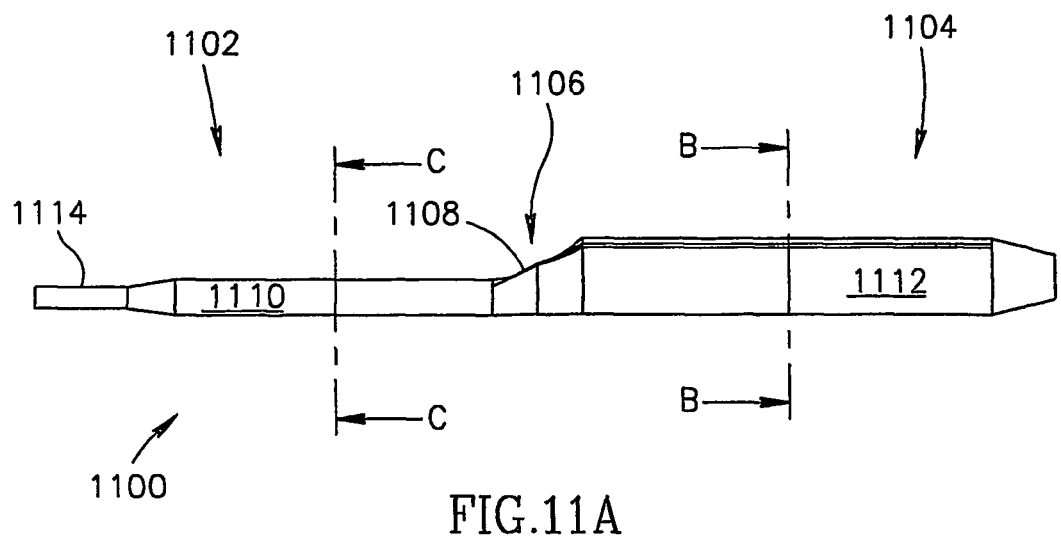
FIG.11A
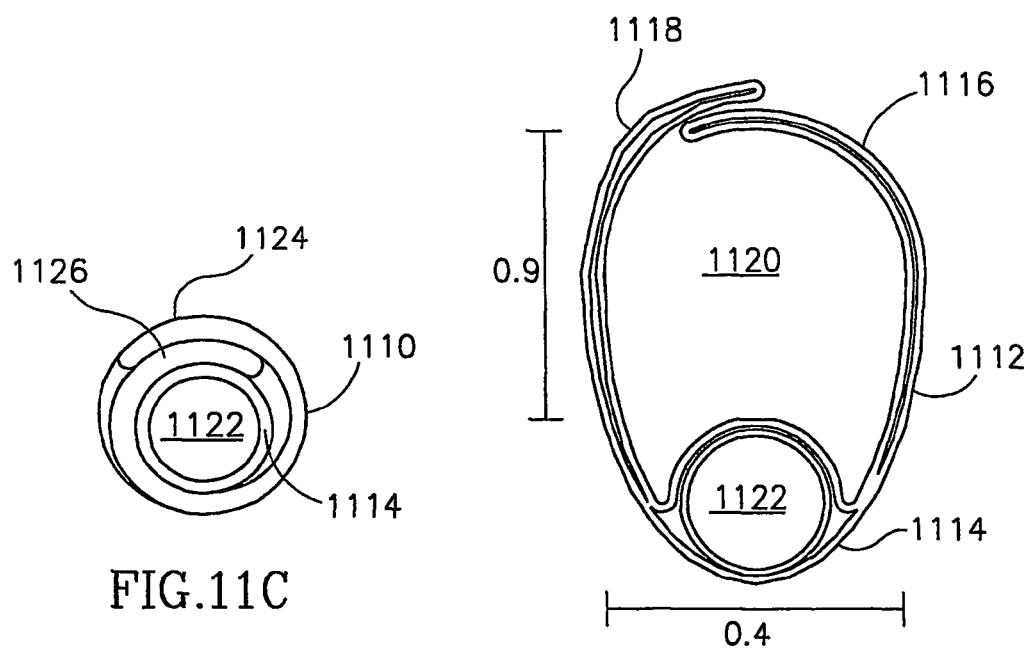
FIG.11C
FIG.11B

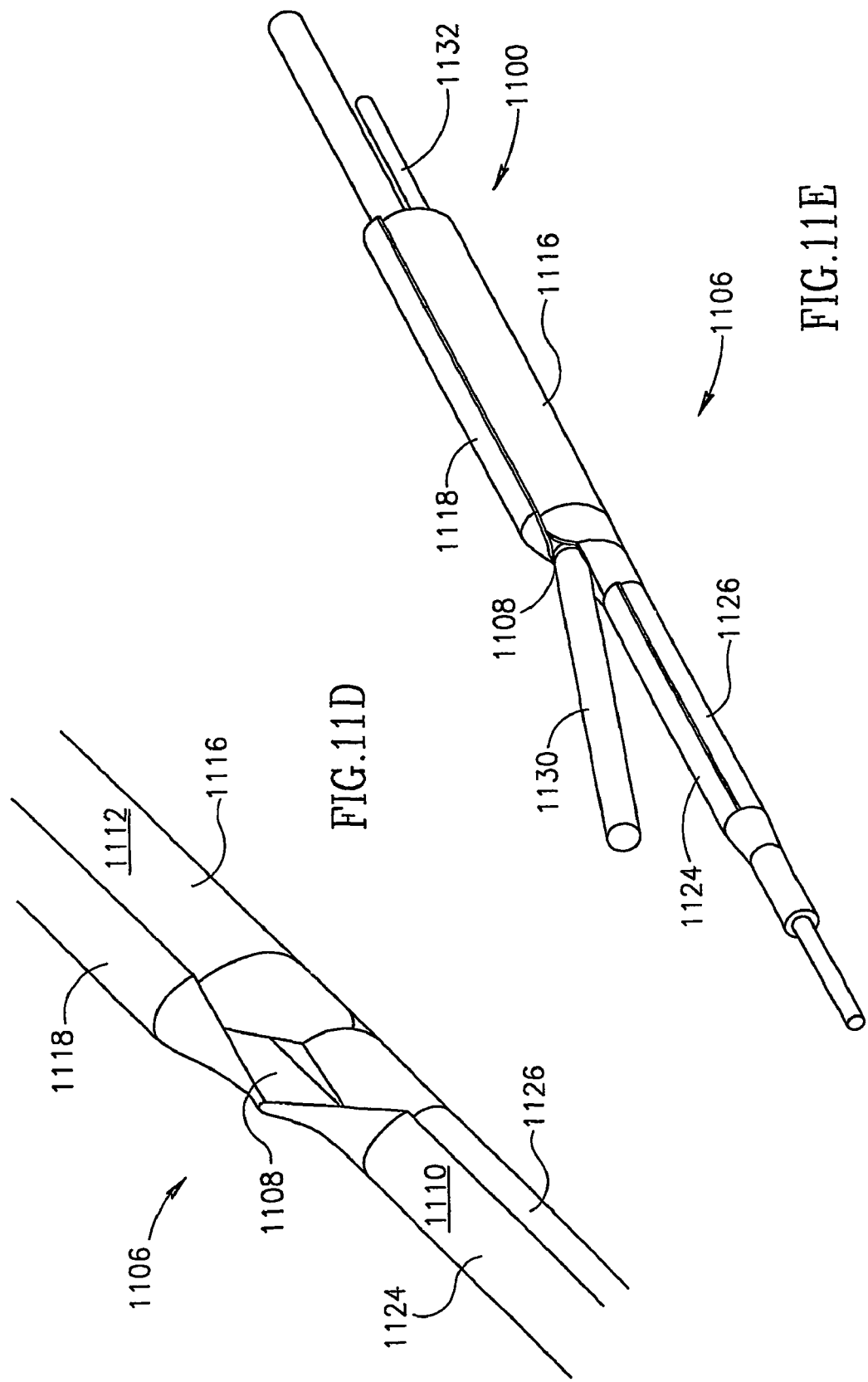

GUIDEWIRE SYSTEM

RELATED APPLICATIONS

The present application is a U.S. National Application of PCT Application No. PCT/IL03/00504, filed on Jun. 12, 2003. The Present application also claims the benefit under 119(e) of 60/387,929 filed Jun. 13, 2002, the disclosure of which is incorporated herein by reference.

FIELD OF THE INVENTION

The present invention relates to intrabody guidewire systems.

BACKGROUND OF THE INVENTION

Clogged arteries are often treated in a minimally invasive manner by the use of a balloon which is inflated at a clogged location and/or using a stent which maintains the patentcy of a clogged location. As a catheter carrying a balloon and/or a stent are often difficult to navigate through the vascular system, and are also difficult to insert into a clogged location, common practice is to first guide a thin guidewire in conjunction with a guide-tube to the clogged location. Often, several guidewires need to be tried until a suitable one is found. The guidewire maybe replaced by a thinner guidewire after the guide-tube reaches the clogged location. A catheter (e.g. a balloon catheter) is then provided over the guidewire and through the tube. As the guidewire is in place, the catheter can be removed and a different catheter, with a different tool provided over the guidewire and optionally through the guide-tube (also known as a guiding catheter). If the guidewire needs to be replaced, it can be exchanged in some systems, for example, using the guide-tube, so that the replacement guidewire can follow the same exact path, being guided by the tube. Nevertheless, since guidewires are long (~2 meters) such exchange is a time consuming process.

Various guidewire-catheter systems have been devised, included, for example systems in which the guidewire is contained in a passage along the catheter (e.g., U.S. Pat. No. 5,324,269), systems in which the passage is partial (e.g., U.S. Pat. Nos. 5,468,225 and 5,554,118) and a system in which the passage is defined as part of a balloon (e.g., U.S. Pat. No. 6,007,517). The disclosure of all of these patents is incorporated herein by reference.

US patent publication 2002/0032457A1, the disclosure of which is incorporated herein by reference, describes a catheter in which a balloon portion can be exchanged without replacing the catheter.

U.S. Pat. No. 5,195,978, the disclosure of which is incorporated herein by reference, describes a catheter in which a guidewire can be rapidly removed from the catheter by tearing a portion of a catheter guidewire channel off, outside of the body. In U.S. Pat. No. 5,472,425, the disclosure of which is incorporated herein by reference, the guidewire itself tears the channel open, again, apparently outside the body and the guidewire may also be used to create an exit port from the catheter at a chosen location. However, there is no suggestion or reason for creating an exit at the balloon.

One complicated situation is that of a bifurcation stent implantation. Here, two guidewires are generally provided, one for each side of the bifurcation. U.S. Pat. No. 6,325,826 and US patent application publication 2001/0049548 A1, U.S. Pat. No. 6,210,429, WO 00/74595 and WO 99/36002, the disclosures of which are incorporated herein by reference, describe various two guidewire systems. All of these systems, however, seem to require a guidewire sheath for each guidewire, as a separate catheter, as a separate sheath inside a stent to be deployed or as a previously extended sheath. This may add undesirable complexity or thickness to the delivery system. Balloons for the two branches are inflated sequentially, one after the other is retracted.

SUMMARY OF THE INVENTION

An aspect of some embodiments of the invention relates to a tool carrying catheter adapted to be mounted on one or two guidewires, such that at least one guidewire exits non-axially from a middle of the vascular treatment tool. In an exemplary embodiment of the invention, the tool is a balloon or a stent. In various embodiments, the tool and/or the catheter itself are modified to allow the exiting of the guidewire in the middle of the tool. In an exemplary embodiment of the invention, the tool is a balloon, which is split, for example, in an axial or trans-axial direction and the catheter (or balloon) comprises a guidewire channel with an opening in the middle of the balloon.

In an exemplary embodiment of the invention, two guidewires are provided and they are first guided to the desired location and then the catheter with the tool is guided over the guidewires. Optionally, a tool for one branch of the bifurcation is guided over a guidewire after the catheter with the tool for the other branch is guided over the other guidewire.

In an exemplary embodiment of the invention, no separate sheath, catheter, and/or pre-projection are required for the second guidewire. The second guidewire may be pre-extended or may be extended after the catheter is at a target location.

In an alternative embodiment of the invention, both guidewires exit from the middle. Optionally, only a single guidewire is provided, and that guidewire exits from the middle of the tool in a non-axial direction An aspect of some embodiments of the invention relates to a catheter that carries a first tool and which is adapted to have a second tool provided in a radial direction to catheter and through the first tool. In an exemplary embodiment of the invention, the first tool includes an opening for passing the second tool. Optionally, the second tool is provided after the first tool is at least partially deployed, so that an aperture in the side of the first tool is large enough to pass the second tool. Optionally, the second tool is provided on a guidewire which may be, for example, provided through the first tool before the deployment, or after the deployment.

Optionally, the catheter and/or first tool guide the guidewire and/or the second tool to a desired deployment location.

An aspect of some embodiments of the invention relates to a stent adapted to provide a channel for a guidewire. In an exemplary embodiment of the invention, the stent is crimped on a balloon and the channel is defined between the stent and the balloon. Alternatively the channel is defined wholly with the stent. Optionally, the stent is self-expanding.

In an exemplary embodiment of the invention, the channel is canceled by the expansion (e.g., self or assisted) of the stent.

In an exemplary embodiment of the invention, the channel protrudes from a profile of the stent. Alternatively, the channel is within a profile of the stent.

In an exemplary embodiment of the invention, the channel is defined along the entire stent. Alternatively, the channel is defined only along a part of the stent. Optionally, the channel openings are defined to aim the guidewire in a desired direction.

In an exemplary embodiment of the invention, the channel is adapted for threading of the stent onto an inserted guidewire. Alternatively or additionally, the channel is adapted for threading a guidewire into the channel after the stent is in the body. In an exemplary embodiment of the invention, the channel includes a beacon, such as a magnetic marker, for guiding a magnetic field sensor guide wire into the channel.

An aspect of some embodiments of the invention relates to a device for mounting a stent onto a balloon, such that a guidewire channel is formed by the stent. In an exemplary embodiment of the invention, the device comprises a form with a depression that matches a desired outer profile of the guidewire channel. Optionally, two sets of devices are provided, one for initial forming and crimping and a second for final crimping of the stent onto or into a delivery catheter.

An aspect of some embodiments of the invention relates to a stent carrying balloon catheter in which all of the guide wires used by the balloon (e.g., one, two or more) are carried between the balloon and the stent or by the stent, without requiring the definition of a dedicated channel for a guide wire in the balloon catheter. In some cases, one or more guide wires may be carried by the balloon itself, with or without assistance from the stent (if any). The guide wire channels thus defined by the balloon and/or stent may be for the entire length of the balloon or may include an entry or an exit near a middle of the balloon.

An aspect of some embodiments of the invention relates to a method of adapting a stent for crimping in a manner which will form a channel. In an exemplary embodiment of the invention, the stent is weakened at the channel forming parts. For example, the material of the stent may be thinned or the widths of stent parts may be reduced. Alternatively or additionally, the stent may be annealed or otherwise heat treated.

An aspect of some embodiments of the invention relates to a stent in which a portion of the stent is crimped or bent out of the plane of the stent, for example prior to implantation. In an exemplary embodiment of the invention, the in plane and out of plane portions are interconnected by one or more torsion bars defined in the stent, for example, axial torsion bars. In an exemplary embodiment of the invention, the use of torsion bars allows a greater amount of distortion to be provided in the stent, without the distortion being irreversible by the deployment of the stent. In an exemplary embodiment of the invention, the torsion bars (and/or other modifications of the stent, for example annealing) are defined in locations that match a later expected crimping of the stent. Optionally, the stent includes a slot at one end, to assist in proper orientation in a crimping mechanism, for example which may include a matching nub. Alternatively or additionally, other alignment methods may be used, for example visual methods.

An aspect of some embodiments of the invention relates to a stent design for providing a channel in the stent. In an exemplary embodiment of the invention, the stent comprises a mesh like structure with multiple links on its surface. In one embodiment, only non-sequential links are selected to form the channel. Alternatively or additionally, links at the ends of the channel are bent, to guide the guidewire that passes through the channel and/or to prevent scratching of an enclosing blood vessel.

An aspect of some embodiments of the invention relates to a method of adapting an existing stent to have an exit along its length. In an exemplary embodiment of the invention, at least one link (or other part) of the stent structure is cut, for example, using a laser cutter or a water cutter, to provide the stent with a side aperture. Optionally, a plurality of radially placed portions are cut out, so that the stent can be aligned in several ways. In an exemplary embodiment of the invention, the cut stent is mounted on a delivery system so that the aperture in the stent matches a guidewire channel in the delivery system. However, this is not required, for example, if the guidewire channel is formed in the stent.

In an exemplary embodiment of the invention, the exit along the stent is not a plain aperture and/or does not expand symmetrically around the guidewire. When the stent is conveyed over the guide wire, it is expected that at least in some cases, the stent will advance until the guide wire is in contact with the proximal-most side of the exit and pushed against the distal most side of the bifurcating blood vessel wall. Simple expansion of a standard aperture may cause a significant portion of the aperture to be blocked by a blood vessel wall, instead of being adjacent the bifurcation lumen. In an exemplary embodiment of the invention, the aperture is defined to include a stop at its middle (e.g., with a protrusion from either side of the stent), to prevent the stent from advancing too far on the guide wire. When the aperture is expanded, the stop will be bent away, so that the opening will open in a manner that is asymmetric relative to the location of the guidewire. Alternatively or additionally, the aperture is defined to expand in an asymmetric manner. This aspect of some embodiments of the invention may be used, for example when crimping an existing stent and when designing a new stent.

An aspect of some embodiments of the invention relates to using a balloon for centering and/or expanding a side exit aperture of a bifurcation stent. In some cases, even if a stop is provided in the stent, the aperture may be misaligned and/or it may be difficult to push a balloon catheter through it, for example with the catheter getting stuck on the stop. In an exemplary embodiment of the invention, the guidewire in the side vessel is a balloon guidewire or a balloon catheter which is retracted to straddle the aperture and expanded to align and/or open the aperture. Such alignment may be by changing the aperture shape and/or by moving the stent in which the aperture is formed. If only alignment is required, this may be provided by advancing a balloon catheter over the guidewire prior to providing a stent in the side vessel. In an exemplary embodiment of the invention, the balloon guidewire has a single lumen used for inflation, is generally pliable like a guidewire and has a soft tip or other guide-wire type tip. In an exemplary embodiment of the invention, when a balloon catheter is to be advanced over the guidewire, the balloon part of the guidewire is advanced and then the balloon catheter is advanced. Optionally, the proximal end of the balloon guidewire is detachable from an inflation means (e.g., a syringe). This may be useful when mounting the stent on the guidewire as the channel crimped in the stent may only be able to accommodate the guidewire at non-balloon portions thereof, which may have a slightly greater diameter.

An aspect of some embodiments of the invention relates to a balloon catheter in which the balloon defines a guidewire channel and releases the guidewire when the balloon is inflated. In an exemplary embodiment of the invention, the channel is defined by the folds of the balloon, when it is folded down. Alternatively, the balloon includes an axial slot which defines the channel. The slots stays normally closed, for example, due to a small amount of adhesive, a thin membrane or other connection between opposing sides of the slot. When inflated, this connection is destroyed and the guidewire is released. Alternatively or additionally, the slot is defined by a stiffening of the balloon membrane at the slot position (e.g., by thickening, by adding material and/or surface treatment).

In one example, the stiffening is elongate. In another, the stiffening is at discrete points along the slot. In either case, the stiffening delays opening of the slot until the balloon is inflated with a sufficient pressure. After deflation, the balloon may revert to its previous, slotted, configuration, or not, for example depending on whether the stiffening is elastically or plastically deformed by the balloon inflation.

In some embodiments of the invention the balloon and/or the stent define a channel wide enough for a balloon or other catheter to pass into a side vessel and not only a guidewire, possibly before the channel defining balloon and/or stent are expanded and/or expended fully.

An aspect of some embodiments of the invention relates to a method of rapid exchange of tools on a guidewire. In an exemplary embodiment of the invention, a plurality of tools are mounted on the guidewire in a sequential order (e.g., inside the body and/or outside the body), each tool being connected to the guidewire only on a relative short length of channel in the tool. The channel is formed with a tear strip or area, so that when the tool is retracted, for example over a next tool in line, over a thickening in a guidewire on which the tool rides and/or over a tube, the channel is torn and the tool can be retracted. The next tool in line can be advanced, possibly independently of the removal of the first tool.

An aspect of some embodiments of the invention relates to a method of rapid exchange of catheters, in which a guidewire is torn out (or released) of part or all of a guidewire channel in a catheter, while it is inside the body. In an exemplary embodiment of the invention, the catheter is then pulled off the guidewire while not connected to the guidewire. Optionally, the channel includes a weakened part, for example along the length of the catheter or at its distal end, depending on where the guidewire is connected (e.g., only adjacent distal end, along catheter length or at any other point along catheter).

An aspect of some embodiments of the invention relates to a method of implanting stents in a bifurcation area. In an exemplary embodiment of the invention, a first stent is provided to a main branch of the bifurcation area, straddling a side branch of the bifurcation. A second stent is provided through the first stent to the side branch. Optionally, the two stents are inflated at a same time, optionally at least during a final inflation of the stents. In an alternative embodiment, the stent in the main path comprises two axially displaced stents, which are optionally expanded using a single long balloon.

An aspect of some embodiments of the invention relates to a guidewire guide for use outside the body. In an exemplary embodiment of the invention, the guide comprises two channels, one for a guide wire and one for a catheter with a guide wire. The guide, which may for example clip onto the catheter is optionally used to prevent the guidewire from curling away from the catheter and distorting the crimped guidewire channel formed in the stent.

An aspect of some embodiments of the invention relates to providing a stent, for example of the designs described herein or of any stent design known in the art, made of titanium or a titanium molybdenum alloy. In an exemplary embodiment of the invention, due to the greater strength of titanium, the struts of the stent are made narrower and/or thinner.

An aspect of some embodiments of the invention relates to plastically deformed stents in which spring back is reduced, for example, stents made of titanium or titanium alloy. In an exemplary embodiment of the invention, the stent is constructed so that most of the stress related to distortion is concentrated in certain areas of the stent. Other parts of the stent, which might otherwise contribute to spring-back are made harder or thicker. In one example, the entire stent is hardened and plastically distorting parts are softened, for example using a heat or chemical treatment. In another example, the stent comprises ribbon like parts and the sharp bends of the ribbons are made thinner (or other parts thicker, for example in one or two dimensions) so that the stress concentrates there. Alternatively or additionally, elastically distorting sections of the stent are made shorter, so that they will experience less actual elastic distortion.

There is thus provided in accordance with an exemplary embodiment of the invention, a tool-carrying catheter, comprising:

an elongate body adapted for insertion into a blood vessel;

a tool section attached to a distal side of said body, and a guide-channel adapted to carry at least a guide-wire, wherein said catheter includes an entry port into said guide-channel for said guide wire and wherein said tool includes a distal exit for said guide wire from said guide-channel, defined in a side of said tool. Optionally, said entry port is proximal to said tool. Alternatively, said entry port is distal to said tool.

In an exemplary embodiment of the invention, said guide-channel is adapted to carry a second catheter. Optionally, said second catheter is a balloon catheter.

In an exemplary embodiment of the invention, said guide-channel is limited to a distal section of said elongate body.

In an exemplary embodiment of the invention, the catheter comprises a second guide-channel adapted to carry a second guide wire. Optionally, said two guide-channels share a common lumen section. Optionally, said second guide-channel defines an aperture in its side for said distal exit.

In an exemplary embodiment of the invention, said tool comprises a balloon. Optionally, said guide-channel is defined through said balloon. Alternatively or additionally, said guide-channel is defined between folds of said balloon. Alternatively or additionally, said balloon includes a stiffing which defines said guide-channel. Alternatively or additionally, said balloon includes adhesive which adheres two parts of said balloon to define said guide-channel. Alternatively or additionally, said balloon is split to define said channel between two sections of said balloon. Optionally, said balloon is axially split. Alternatively or additionally, said balloon is trans-axially split.

In an exemplary embodiment of the invention, said tool comprises a stent. Optionally, said stent is mounted on a balloon. Optionally, said guide-channel is defined between said stent and said balloon. Alternatively or additionally, said guide-channel is defined between folds of said balloon. Optionally, said guide-channel is wide enough to accommodate a second balloon catheter.

In an exemplary embodiment of the invention, said guide-channel is defined by a crimping of said stent. Alternatively or additionally, said stent includes a dedicated aperture along its length for said exit port. Alternatively or additionally, said stent defines two guide-channels.

There is also provided in accordance with an exemplary embodiment of the invention, a guiding stent comprising a stent body crimped in a radially non-uniform manner to define at least one guide-channel adapted to carry at least a guide-wire. Optionally, said channel is designed to accommodate only a single guidewire. Alternatively, said channel is designed to accommodate a plurality of guidewires.

In an exemplary embodiment of the invention, said channel does not extent along an entire length of said stent. Alternatively or additionally, said channel is adapted to carry a balloon catheter.

There is also provided in accordance with an exemplary embodiment of the invention, a stent comprising:

an elongate cylindrical body; and an aperture defined in a middle section of said body, said aperture including two abutting sections, one of said sections being narrower than the second section at least at said junction. Optionally, said stent is defined by a plurality of circumferential expandable bands inter-linked by a plurality of axial links. Optionally, said stent has a regular pattern and wherein said aperture is defined by the lack, in said pattern, of one axial link and by the lack of a section of an expandable band between two axial links. Alternatively or additionally, said axial links include at least one protrusion and wherein axial links abutting said aperture are configured to have their protrusion point away from said aperture.

In an exemplary embodiment of the invention, said stent is adapted to be placed in a target vessel having a varying diameter along the length of the stent and wherein the aperture is narrower towards an end of the stent adapted to be in a narrow wider section of the target vessel. Alternatively or additionally, said junction is adapted to be obliterated by expansion. Alternatively or additionally, said aperture is configured to allow passage of an unsheathed balloon catheter passing through it, without snagging of the balloon. Alternatively or additionally, said stent is adapted to radially expand more in a portion of the stent to one side of the aperture than in a portion of the stent to the other side of said aperture.

There is also provided in accordance with an exemplary embodiment of the invention, a method of folding a balloon to form a channel, comprising:

(a) providing a balloon catheter having a balloon folded over said catheter;

(b) providing an elongate element between said folds and said balloon, along at least a part of an axial section of said balloon;

(c) providing said elongate element with a bend; and (d) manipulating said elongate element such that said bend moves in a proximal direction and travels along a contact area between said folds;

(e) refolding said at least a part of balloon, if said moving of said bends unfolded said balloon. Optionally, the method comprises holding a proximal portion of said balloon to prevent its unfolding during said manipulating.

In an exemplary embodiment of the invention, manipulating said element comprises pulling back a proximal side of said elongate element. Alternatively or additionally, manipulating said element comprises pulling back a distal side of said elongate element.

In an exemplary embodiment of the invention, the method comprises inserting said elongate element between said folds after folding of said balloon over itself. Alternatively or additionally, the method comprises folding back said elongate element to form said bend.

In an exemplary embodiment of the invention, folding said balloon comprises partially inflating said balloon, shaping said balloon to have at least two flaps, deflating said balloon, while maintaining said flaps and folding said flaps over said catheter.

There is also provided in accordance with an exemplary embodiment of the invention, a method of crimping a stent on a balloon to define a channel, comprising:

providing a stent over a balloon;

crimping said stent using a mold with having a cross-section which is not radially symmetric for at least part of its length, thereby defining a channel. Optionally, said cross-section is that of a circle with a bulge. Alternatively or additionally, said mold has a circular cross-section for part of its length and a non-circular cross-section for a second part of its length. Alternatively or additionally, the method comprises inserting a stylet form in an axial direction along and within at least part of said stent. Optionally, said stylet exits said stent at a middle section thereof.

In an exemplary embodiment of the invention, the method comprises repeating said crimping with a second mold having a cross-section smaller than said first mold over at least part of its length.

In an exemplary embodiment of the invention, said mold splits along its length.

There is also provided in accordance with an exemplary embodiment of the invention, a method of forming a crimped stent with a channel, comprising:

crimping at least a portion of said stent on a balloon catheter, such that an axial channel remains defined by at least one of said balloon and said stent, within the volume enclosed by said stent, said axial channel having a maximum trans-axial extent; and passing a stylet having a trans-axial extent larger than said maximum trans-axial extent of said channel, through said channel, thereby distorting said stent about said channel. Optionally, said channel is defined between folds of said balloon.

There is also provided in accordance with an exemplary embodiment of the invention, a clip for adjusting guidewires, comprising:

a first jaw and an opposing second jaw and adapted to open by relative rotation about a first axis;

a pair of spaced apart channels defined between said jaws and having a same general direction as said first axis, said channels being sterile and smooth enough to allow slippage of an elongate medical tool only in an axial direction therethrough. Optionally, one of said channels is sized for a catheter and one is sized for a guide-wire. Alternatively, both of said channels are sized for catheters.

In an exemplary embodiment of the invention, said jaws are elastically pre-disposed to close and comprising extensions of said jaws on an opposite side of said axis, which when pressed together open said jaws.

There is also provided in accordance with an exemplary embodiment of the invention, a kit comprising:

a balloon catheter having a stent mounted thereon and defining a channel with an exit in a side of said stent; and a second balloon catheter configured to be passed through said exit. Optionally, said second balloon catheter has a second stent mounted thereon, said stents being configured to cooperate with said stent to provide support to a blood vessel at a bifurcation.

There is also provided in accordance with an exemplary embodiment of the invention, a catheter adapted for quick removal, comprising:

an elongate catheter body, defining a guide-wire channel at a distal end thereof, said channel having a proximal entry port and a distal exit port, wherein said channel defines a weakening therein, which weakening is openable such that said channel is open for release of a guidewire from said entry port to said exit port. There is also provided in accordance with an exemplary embodiment of the invention, a kit including a catheter as described above and including a second catheter having a forward element adapted to tear said channel when it contacts said entry port of said catheter. Alternatively or additionally, such a kit includes a tube adapted to tear said channel when it contacts said entry port of said catheter.

There is also provided in accordance with an exemplary embodiment of the invention, a method of tool removal from a body, comprising:

bringing together a forward tearing element of a proximal device mounted on a guide wire and an entry port of said guidewire in a distal device, by motion of at least one of said proximal device and said distal device;

continuing said bringing together such that said forward tearing element opens a channel of said distal device and disconnects it from said guidewire; and retracting said distal device. Optionally, said opening of said channel comprises tearing. Alternatively or additionally, said bringing together comprises advancing said proximal device, while maintaining a position of said distal device.

There is also provided in accordance with an exemplary embodiment of the invention, a method of implanting a stent in a bifurcation, comprising:

placing two guidewires, one into each of two branches of a bifurcation;

mounting a stent on said two guide wires such that at least one guide wire exits through an aperture in a side of the stent; and deploying said stent to engage a blood vessel at said bifurcation. Optionally, mounting comprises mounting after said placing. Alternatively or additionally, mounting comprises mounting before placing. Alternatively or additionally, the method comprises providing a balloon catheter into a side vessel of said bifurcation after at least roughly positioning said stent in another side vessel of said bifurcation and prior to deploying said stent.

Alternatively or additionally, the method comprises providing a balloon catheter into a side vessel of said bifurcation after positioning said stent in another side vessel of said bifurcation and after deploying said stent.

Alternatively or additionally, the method comprises providing a balloon catheter into a side vessel of said bifurcation after positioning said stent in another side vessel of said bifurcation and partially expanding said stent.

Alternatively or additionally, the method comprises expanding a balloon catheter in a side vessel of said bifurcation to assist in positioning said stent in another side vessel of said bifurcation.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIGS. 3A-3E show schematic side, front cross-section, plan and detail views of a crimped stent in accordance with an exemplary embodiment of the invention;

FIGS. 4A-4F illustrate a crimping device and a corresponding crimped stent in front cross-sectional and side views, in accordance with an exemplary embodiment of the invention;

FIGS. 8A-8D illustrate guidewire releasing balloons in accordance with exemplary embodiments of the invention;

FIGS. 11A-11E illustrate a balloon folding method in accordance with an exemplary embodiment of the invention.

DETAILED DESCRIPTION OF EXEMPLARY EMBODIMENTS

Figure 1:
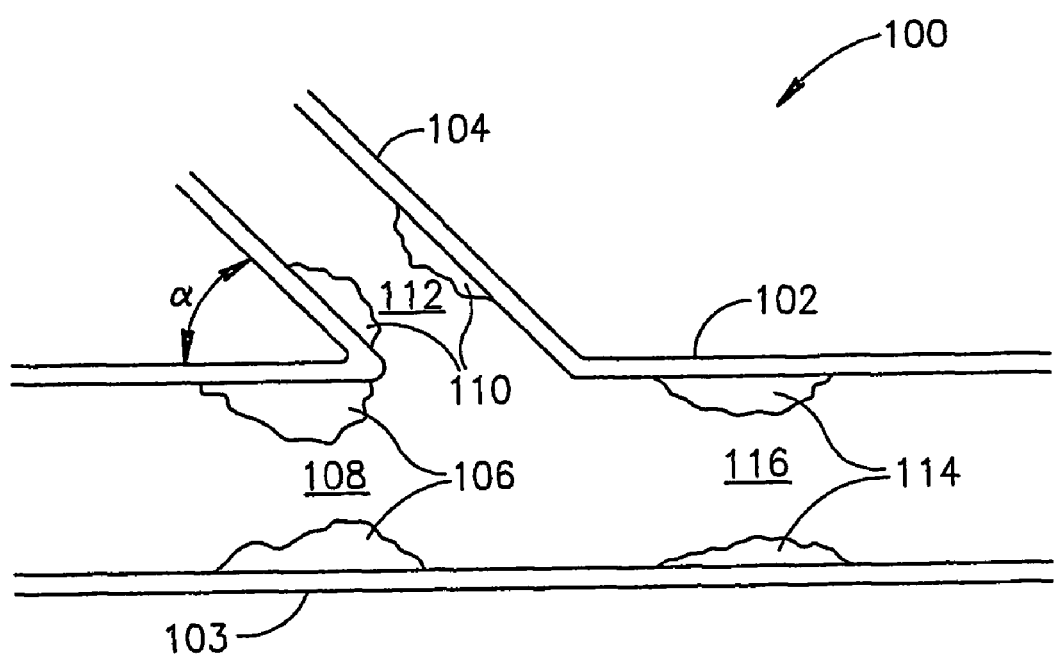
FIG. 1 shows a narrowed vessel bifurcation, which may be treated using methods and devices in accordance with exemplary embodiments of the invention.

FIG. 1 shows a narrowed vessel bifurcation 100, which may be treated using methods and devices in accordance with exemplary embodiments of the invention. Typically, such a bifurcation comprises a main vessel 102, continuing as a main branch 103 with a branching-off side branch vessel 104, at an angle α. Vessels 102-104 may be, for example veins, arteries and/or grafts. In addition, in some cases, one or both branches are narrower than vessel 102. Different body portions and different people have different angles between the branches, for example, in the connection of cardiac arteries to the aorta, an angle α of 90° may exist.

Bifurcation 100 is shown narrowed at main branch 103, by plaque (or other narrowing source) 106, which creates a narrowed lumen 108. Alternatively or additionally, plaque 110 may create a narrowed lumen 112 in side branch 104 and/or plaque 114 may create a narrowing 116 in vessel 102.

Many stenosis amelioration tools exist for treating such narrowings, including, for example, plaque removing tools, such as ultrasonic and laser catheters and rotating ablators and tools for moving plaque out of the way (and optionally compressing it), such as stents and/or balloons. In addition, other tools that are provided by catheter of guidewire, possibly for treating other pathologies, may be used.

FIGS. 2A-2F illustrate a process for treating the narrowed bifurcation of FIG. 1, using a guidewire channeling stent in accordance with an exemplary embodiment of the invention.

In these figures, plaque 110 and 108 are shown. However, this method can be used also for substantially any other plaque configurations.

Figure 2A:
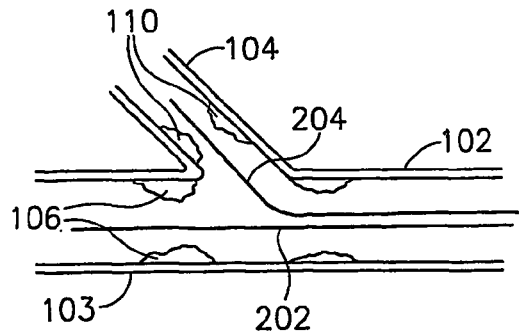
FIGS. 2A-2F illustrate a process for treating the narrowed bifurcation of FIG. 1, using a guidewire channeling stent in accordance with an exemplary embodiment of the invention.

In FIG. 2A, two guidewires, 200 and 202, are provided in the branches 103 and 104, so that they lie in the narrowings 108 and 112. In an exemplary embodiment of the invention, a single guide-tube (not shown) is used in conjunction with providing both guidewire to the bifurcation, at which point each guide wire may be advanced into a different side of the bifurcation and optionally replaced by a thinner guidewire. While a standard guide-tube may be used, optionally, the guide-tube has a non-circular cross-section, for example an elliptical cross-section, to match the non-circular cross-section of a stent in accordance with some embodiments of the invention.

Figure 2D:
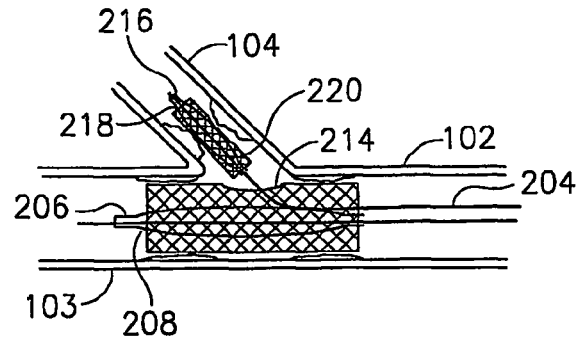
Figure 2B:
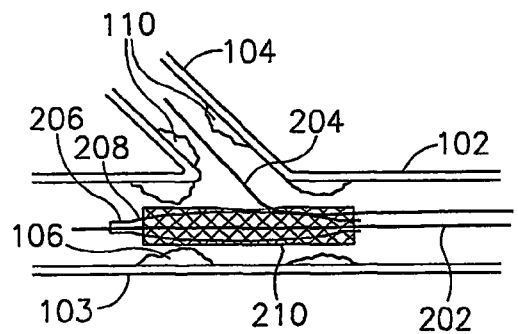

In FIG. 2B, a first balloon catheter 206 is provided over the two guidewires so that a balloon portion 208 and a stent 210 mounted on the catheter lie in narrowing 108. As shown in the figure, guidewire 204 exits from catheter 206 at its middle. In this embodiment of the invention, guidewire 204 is mounted in a channel formed by stent 210. In an alternative embodiment of the invention, described below such a channel is formed between the stent and the balloon. In another embodiment described below, the channel is formed in the balloon itself. In another embodiment described below, the channel is in the catheter and there is a side exit for the guidewire through the balloon portion of the catheter.

Figure 2E:
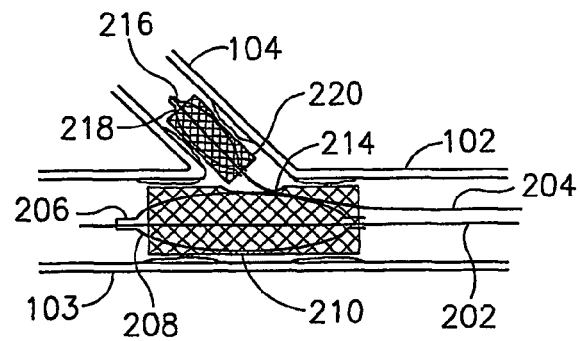
Figure 2C:
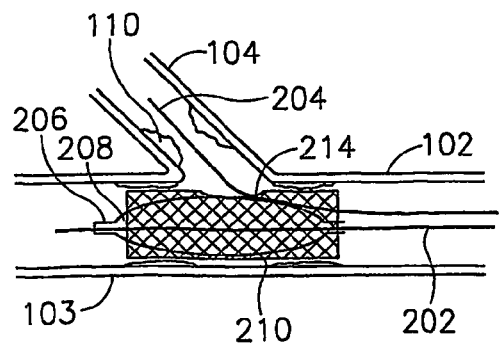

In FIG. 2C, balloon 208 is inflated, so that stent 210 expands. In an exemplary embodiment of the invention, this expansion compresses plaque 106. In some exemplary embodiments of the invention, this expansion is not a final expansion of stent 210, as described below, however, in other embodiments, this is a final, maximal expansion.

While stent 210 is shown mounted on balloon 208, in an alternative embodiment of the invention, a regular balloon catheter may be brought over guidewire 202 (optionally not over guidewire 204 as well), the balloon inflated and then replaced with catheter 206 with stent 210 mounted thereon, or a different type of catheter, for example a shape-memory stent or elastic (or super elastic) stent deploying catheter.

At FIG. 2D, a second balloon catheter 216 is brought over guidewire 204, through an opening 214 in stent 210. Optionally, balloon 208 is at least partially deflated and/or moved axially for this passage. Alternatively or additionally, balloon 208 has a design that provides an increased through channel when it is inflated, for example as used in some perfusion balloons, for example the one described in U.S. Pat. No. 5,549,555, the disclosure of which is incorporated herein by reference and in the above referenced U.S. Pat. No. 6,007,517.

At FIG. 2E, balloon 218 is inflated, fixing stent 220 in place. Optionally, balloons 208 and 218 are inflated at a same time, for example to ensure that stent 220 does not over expand and/or to finalize the deployment of stent 210. Alternatively or additionally, balloon 218 may be inflated first, at least to a partial extent. In one example, such partial inflation, especially if part of balloon 218 remains in opening 214, ensures that the shape and/or location of opening 214 conforms to the location of side vessel 104 and/or the deployment of stent 220. Optionally, stent 210 is plastic enough to be properly distorted by balloon 208, does not include balloon piecing points around opening 214 and/or is not fixed firmly in place so such inflation can align it radially and/or axially relative to branch vessel 104. Alternatively or additionally, balloon 208 remains at least partially inflated during this partial inflation of balloon 218, to prevent inward collapse of stent 210. Alternatively or additionally, balloon 218 is defined with a recess to receive the proximal side of balloon 218 when it inflated. In one example, this recess is defined by gluing balloon 208 using a bond that will tear only when sufficient pressure is applied (e.g., the maximal inflation pressure for final fixation of stent 210). At lower pressures, balloon 208 will not inflate completely at the bond point, defining the above recess.

It should be noted that the order of provided catheters 206 and 216 may be reversed, as may be the order of treating narrowings 108 and 112.

In an exemplary embodiment of the invention, stent 220 is longer than shown (or otherwise positioned), so that it can overlap in vessel 102, at one or more points, possibly along its circumference. Optionally, catheter 216 and stent 220 are provided before catheter 206 and stent 210, so that the side stent 220 is expanded first. Then the expansions of balloon 208 and/or side stent 210 flatten the rim of stent 220 so that it does not protrude. While a mesh stent may be used for stent 220, in an exemplary embodiment of the invention, a stent with a pre-defined flaring portion is used. Various flaring ostial stents are described, for example in U.S. Pat. Nos. 6,293,964 and 5,868,777 and WO publication WO 97/17101, the disclosures of which is incorporated herein by reference.

One potential advantage of using some of the exemplary embodiments of the invention is that a regular balloon may be used for delivering stents, possibly even ostial stents. Possibly, the inflation of balloon 208 is in steps, for example, first being positioned only adjacent the proximal part of stent 220, to flattening one side of the rim and then positioned more distally in vessel 102 (branch 103), to flatten the distal rim. The side rims may be flattened when deploying stent 210. It is noted that in some embodiments of the invention, no stent 210 (or stent 220) is provided.

In some embodiments of the invention, balloon 218 has a form that fills the peaked cylindrical volume defined between stent 220 and opening 214. Alternatively, a standard shaped balloon is used, which is optionally, for example during a first inflation, at least partially straddling opening 214.

Figure 2F:
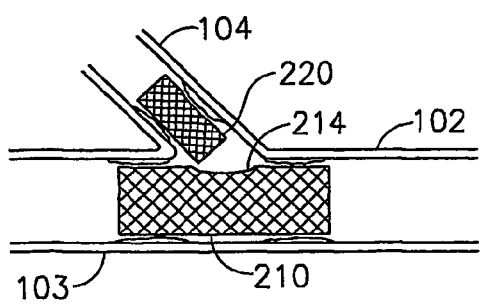

At FIG. 2F, the guidewire and balloon catheters are removed and a stented bifurcation remains.

In the above description, the first step is providing the two guidewires 202 and 204. In other embodiments of the invention, however, this is not required. For example, in one embodiment of the invention, guidewire 204 is provided (e.g., along a separate channel) after catheter 206 (or other tool) is in place. In an exemplary embodiment of the invention, guidewire 204 is pre-bent so that when it is advanced out of catheter 206 (e.g., in one of the various methods described herein), it will bend away from the catheter towards branch 104. Alternatively or additionally, the channel is pre-bent to point in a direction having a significant radial component (relative to the axis of stent 210). Optionally, catheter 206 is rotated to align the tip of guidewire 204 with vessel 104. This alignment and/or the positioning described herein may be viewed, for example, using a fluoroscope.

In some alternative embodiments of the invention, only a single guidewire is provided. In one example, there is no bifurcation and the guidewire is provided outside of catheter 206, for example, for mechanical reasons such as to reduce its diameter and/or increase its flexibility. In this embodiment, the guidewire may exit in a radial direction, possibly distally of the balloon. In another example, there is a bifurcation, balloon 208 has a diameter too large to enter side branch vessel 104 and guidewire 204 optionally exits in a radial direction. Thus, when catheter 206 is advanced over guidewire 204, it slips past vessel 104 and aligns as shown in FIG. 2B (without guidewire 202). This method may be used, for example in vessels that branch away from the aorta, for example coronary arteries.

In another example, guidewire 202 is retracted from a position where it exits forward and then advanced so that it exits to the side. In one example, the guidewire channel includes an opening in its side and the guidewire is pre-bent. However, during initial insertion, the guidewire is rotated so that it is not aligned with the opening in the side. In another example, the guidewire channel in catheter 206 is wider up to the point where the channel branches to the side. Thus, repeated retractions and advancements will tend to result in some cases where the guidewire exited to the side and some where it exist forward. Such a guidewire channel with a narrowing may also be useful for ensuring that a second guidewire will exit to the side, if a forward path is largely blocked by a first guidewire. Multiple branches may be provided along the channel, for example to support multiple exit positions and/or angles. In another example, the guidewire channel is compressible at its distal end. When balloon 208 is inflated, the guidewire cannot be advanced and is forced to exit to the side.

Figure 2G:
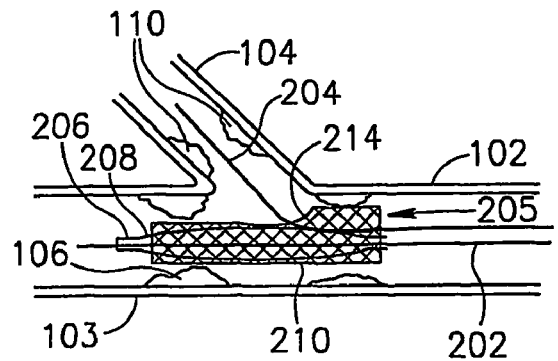
FIGS. 2G and 2H illustrate a process in which the stent includes a wider channel, in accordance with an exemplary embodiment of the invention.
Figure 2H:
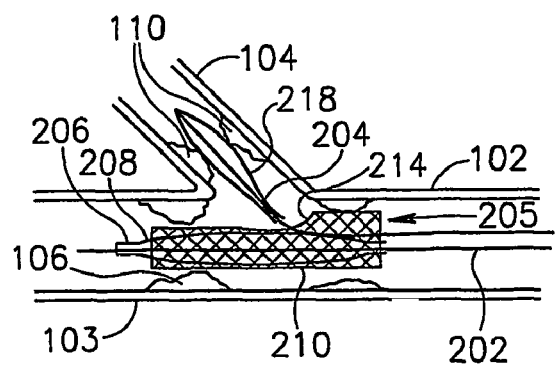

FIGS. 2G and 2H illustrate a portion of a procedure in which balloon 218 is provided through stent 210 before balloon 208 is expanded. In contrast to what is shown in FIG. 2B, in which a minimum diameter channel is provided for guidewire 204, for example of diameter of 0.4 mm or less, in FIG. 2G a substantial channel 205 is provided, having a diameter, for example of diameter 1 mm or an average diameter (for an elliptical channel) of 0.6 mm. In an exemplary embodiment of the invention, channel 205 is wide enough to allow the passage of a balloon catheter even when stent 21 is un-expanded. The cannel may be, for example, within the balloon, defined by folds of the balloon, be a separate tube coupled to the balloon and/or between the balloon and the stent.

FIG. 2H shows balloon 218 passed through opening 214. In an exemplary embodiment of the invention, expansion of balloon 218 helps align opening 214 with side vessel 104. Alternatively or additionally, balloon 218 expands opening 214 to allow passage of stent 220. While balloon 218 is shown without a mounted stent 220, in some embodiments, such a stent is mounted. Alternatively or additionally, balloon 218 is retracted and then a new balloon catheter with a stent is provided. Alternatively or additionally, catheter 216 includes balloon 218 and proximal to it, a second balloon with a stent, for advancing after the inflation of balloon 218. Alternatively or additionally, the mechanism shown in FIG. 9 may be used to removed balloon 218 after its inflation and before provision of stent 220.

FIGS. 11 and 12, described below, show an exemplary balloon and stent configuration in which a substantial channel 250 may be provided.

Figure 2I:
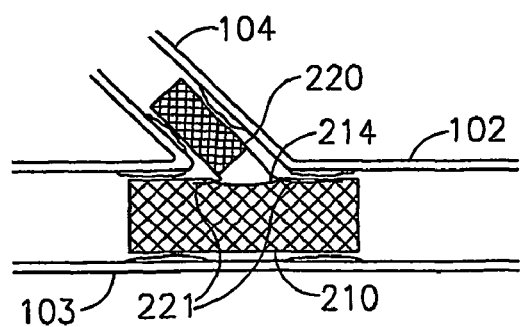
FIG. 2I illustrates the compression of ostial edges of one stent by another, in accordance with an exemplary embodiment of the invention.

FIG. 2I shows a rim 221 of stent 220 which is compressed against stent 210 by the action of balloon 208 which is inflated after stent 220 is placed. Alternatively, stent 220 may be expanded first, for example, after the acts of FIG. 2H and before the acts of FIG. 2C, in which case rim 221 will be between stent 210 and the vessel wall.

Referring to FIGS. 2A and 2B, in some cases the guidewires may be tangled with each other (cross-over). In some embodiments of the invention, the two guide wires are provided into the same vessel, for example vessel 102 or vessel 104 The balloon with stents is advanced over the guidewires, thereby untangling the guidewires, in some cases. In one embodiment, the balloon with stent is correctly positioned and then the side guidewire is retracted back to the bifurcation point and advanced into vessel 104. In another embodiment, once the guidewires are de-tangled, the balloon with stent is retracted and then the guidewires repositioned (e.g., one to each vessel. In the second embodiment, it may be advantageous to originally place both guidewires in the side vessel, as repositioning a guidewire into the main vessel may be easier than repositioning into a side vessel.

Stent 220 can be, for example, a perpendicular opening stent as defined in U.S. provisional application 60/387,930, filed Jun. 13, 2002 and in a PCT application filed by the same assignee and on even date with this application in the Israel patent office acting as a receiving office, the disclosures of which are incorporated herein by reference.

FIGS. 3A-3E show schematic side, front cross-section, plan and detail views of a crimped stent 300, suitable for example for use in the method shown in FIG. 2, in accordance with an exemplary embodiment of the invention.

Figure 3A:
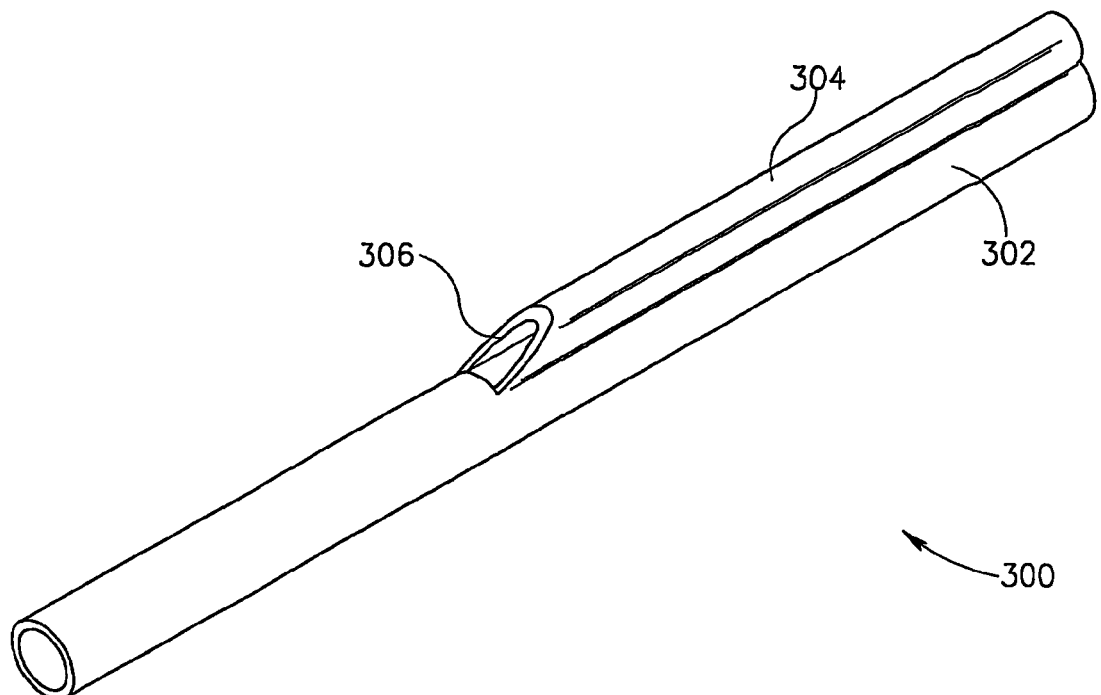

FIG. 3A shows an isometric side view of stent 300. The texture of the stent (e.g., mesh) is ignored and not shown in this figure. As shown, stent 300 includes a main body 302 and a guidewire channel 304, which in this embodiment, ends near the middle of the stent. Channel 304 includes an opening 306, which, when expanded may form part of an opening 214 (as shown in FIG. 2). Optionally, opening 306 is inclined, for example, for reducing friction against the surrounding blood vessel and/or to assist in aiming guidewire 204 to a non-axial direction. The relative diameters of body 302 and channel 304 need not be as shown, for example, they may have a diameter ratio of 3:1, 2:1, 1.5:1, 1:1, 1:2 or any smaller, intermediate or larger ratio.

Figure 3B:
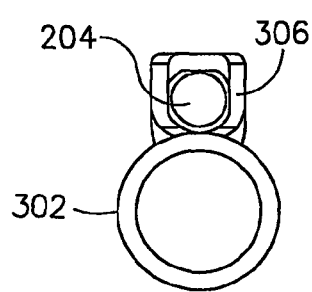

FIG. 3B shows a front view of stent 300, including guidewire 204, for clarity.

Figure 3C:
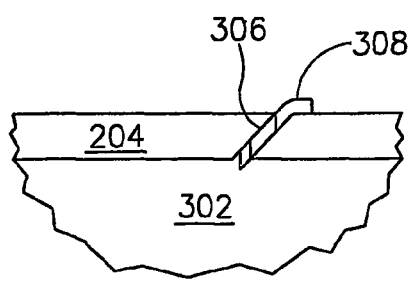

FIG. 3C is a side view of a portion of stent 300 with guidewire 204, showing, a single link 308 of stent 300 being used to form opening 306. In some embodiments of the invention, this single link is the entire channel. Alternatively, at least two such links are provided, for example, to assist in aiming guidewire 204, to reduce friction and/or to prevent undue strains on the single link.

FIG. 3D is a plan view of one possible embodiment of stent 300. In this embodiment, stent 300 comprises a plurality of long link areas 314 which have the form of a folded ribbon. In an exemplary embodiment of the invention, a fold of the ribbon can be used as one of links 308, for forming channel 302. The link areas are connected by at least one area 310 of short recurved segments 312. These segments may also take part in forming channel 302. In an exemplary embodiment of the invention, two short segments cooperate with one ribbon section on either side to define a section of stent 300 that can be expanded to define opening 214. In an exemplary embodiment of the invention, such an opening may be defined at many point along and around stent 300. This may useful, for example, in embodiments where guidewire 204 is aimed by catheter 206 and not by stent 300. Alternatively or additionally, this may be useful to allow stent 300 to be crimped in many orientations and axial positions, for example, for different bodily situations. A particular example mentioned below is when stent 300 serves for supporting a main vessel with multiple side branches along the stent.

Optionally, as shown in FIG. 3E, a single ribbon link 318 may be removed, to assist in crimping and/or in forming opening 214. Alternatively or additionally, link 318 is annealed to soften it for the crimping. Localized annealing is optionally provided at other parts of stent 300, for example for the same reason. PCT publication WO 00/44946, the disclosure of which is incorporated herein by reference, describes a method of local annealing of implants, for example using a feedback controlled e-beam Optionally, stent body 302 is used to assist in aiming guidewire 204. In one example, the first link past link 308 is bent up, to force the guidewire away from stent 300.

Alternatively to forming a channel inside the volume of stent 300, stent 300 may be crimped so that the channel is formed outside the stent. Partial expansion of the stent may be sufficient to release the guidewire. Alternatively, the guidewire may be caught between stent 300 and an underlying balloon. Removal of a link may assist in exiting of the guidewire prior to expansion or after expansion of stent 300.

Optionally, stent 300 includes one or more radio-opaque dots, for example 320 and 322 as shown. These dots may be used, for example to visualize the position and/or orientation of stent 300, as known in the art. In an exemplary embodiment of the invention, these dots are gold that is laser welded onto stent 300.

It should be appreciated that the procedure of deploying stent 300 may use imaging, of any type known in the art, for example fluoroscopy, possibly using contrast material to determine blockage and vessel sizes and/or orientations and/or relative positions of guidewires and vessels.

In an exemplary embodiment of the invention, area 314 comprises a plurality of elongate sections 316. In an exemplary embodiment of the invention, these elongate sections serve as torsion bars when stent 300 is crimped. Optionally, the bars are made longer than shown in FIG. 3D, depending, for example on the degree of distortion caused by the crimping. In an exemplary embodiment of the invention, the torsion bars are made thinner and/or weaker, so that stress caused by the asymmetric crimping is focused on them. Alternatively or additionally, the bars are made long enough and/or strong enough so that they do not buckle and/or distort in a manner that is not substantially overcome by the expansion of the stent during deployment. Exemplary uses of torsion bars for another implant are shown in PCT publications WO 00/56228 and WO 00/56227, the disclosures of which are incorporated herein by reference.

Figure 3F:
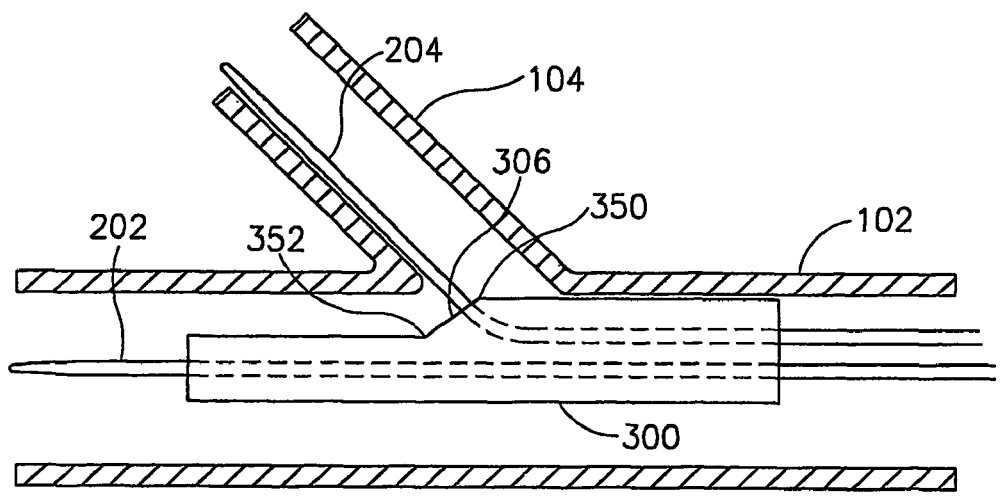
FIG. 3F shows a typical relative placement of a stent in a vessel bifurcation, in accordance with some exemplary embodiments of the invention.

FIG. 3F shows a typical relative placement of a stent 300 in a vessel bifurcation, in accordance with some exemplary embodiments of the invention. In some embodiments, guidewires 202 and 204 are placed first and then stent 300 is advanced over the guidewires. Possibly, this will cause guidewire 204 to be pressed against a proximal side 350 of opening 306, part of opening 306, for example a distal area 352 thereof will be occluded by the wall of vessel 103. After expansion, this might mean that opening 306 is not properly aligned with vessel 104 and/or is too large.

Figure 3G:
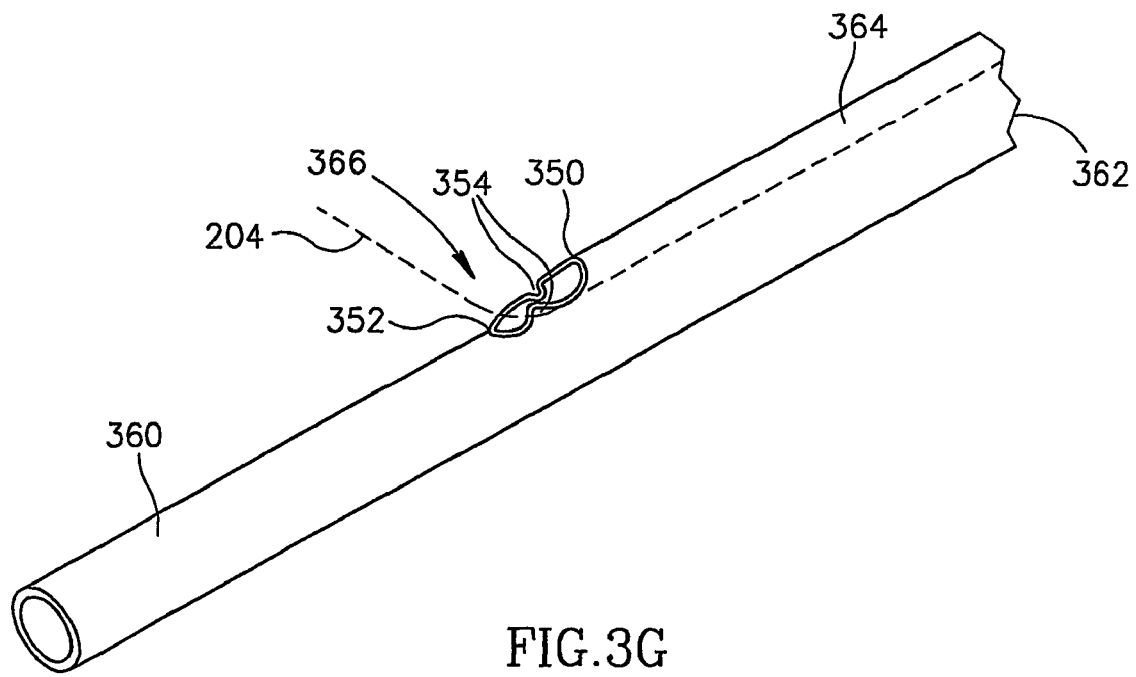
FIG. 3G shows a stopper opening stent, in accordance with an exemplary embodiment of the invention.

FIG. 3G shows a stopper opening stent 360, in accordance with an exemplary embodiment of the invention. In this embodiment of the invention, an opening 366 that is formed in stent 360 is designed to open asymmetrically and/or prevent guidewire 204 from being pushed al the way to proximal area 350. In an exemplary embodiment of the invention, one or more protrusions 354 of stent 360 extend into opening 360 and prevent such movement of the guidewire. However, when the opening is expanded, these protrusions are pushed out of the way and the opening has a suitable shape. Due to the positioning of the guidewire, the positioning of the opening can be as desired, for example aligned with side vessel 104.

In some cases, however, aperture 306 (or 366) may not be correctly aligned. In others, protrusions 354 or the edges of aperture 306 or 366 may prevent easy advance of a balloon catheter (with or without a stent) past the aperture. If the problem is alignment, optionally what is done is provide a stentless balloon catheter along the guidewire and inflate it so the aperture is aligned (e.g., by distorting the stent and/or by moving it). However, as noted it is sometimes difficult to advance a balloon against obstructions. In an alternative embodiment of the invention, guidewire 204 is a balloon guidewire, comprising a tube with a single lumen, for inflating a balloon affixed near its distal end. The tip of guidewire 204 may be any tip known in the art, for example a floppy tip. After (or while) the stent in the main branch is expanded, guidewire 204 is retracted so that this balloon portion is in aperture 306 (or 366). In an exemplary embodiment of the invention, inflating the balloon will then align and/or open the aperture. Guidewire 204 is then advanced and a balloon catheter (or other tool) advanced along it to the side vessel. Typically, retracting a guidewire is easier than advancing it. Possibly, the retraction also pulls back the stent a small amount, making the passage easier.

In an exemplary embodiment of the invention, the balloon guidewire has a minimum diameter, for example as practiced in other guidewires, for example, 14 thousands of an inch (e.g., 0.3-0.45 mm). The balloon portion may have a slightly greater diameter (when inflated) and may be provided, for example, by gluing a membrane over a hole in the tube. In an exemplary embodiment of the invention, the balloon is non-compliant or semi-compliant.

Optionally, the balloon, when inflated or not inflated is used to assist in positioning a tool relative to the stent. For example, the balloon is inflated and then retracted until it is a known distance for the stent. A tool (such as a balloon catheter) is advanced over the guidewire and comes to a stop at the inflated balloon.

Possibly, the extra diameter of the balloon and/or the guidewire tip (e.g., the balloon membrane is tearable) precludes threading the guidewire through the crimped channel in the stent. In an exemplary embodiment of the invention, the proximal portion of the guidewire is detachable from its inflation means (e.g., a syringe or other devices known in the art) so that the guidewire can be threaded backwards through the stent.

It should be noted that in some applications the size constraints are important. Thus, it may be desirable in some embodiments that the crimping of the stent add less to the total device diameter than would a channel in a catheter underlying the stent. In any case, it is desirable in some embodiments of the invention, that the narrowest diameter guidewires be used and the crimping be made minimal as well. This generally means dimensions of, for example less than 0.6 mm or 0.5 mm for the guidewire channel diameter and, in some cases, that only the simplest of guidewires are used. In some embodiments of the invention, it is desirable that the crimped portion of the stent not affect its profile too much. This may mean, for example, that the crimped channel area protrudes less than 50%, 30%, 20% or 10% from the diameter of the stent without the channel crimping. In other embodiments, size constraints are less important. For example, a stent may be crimped in the shape of a FIG. 8 profile, with a balloon catheter in one part and a guidewire channel (or even catheter channel) in another.

FIGS. 3A-3G have focused on applications where one guidewire is provided in a standard manner and one is provided using a path defined by crimping a stent. However, it should be appreciated that these methods (and other described herein) may be used to avoid providing any guidewire channel in the balloon, e.g., in a standard manner. These methods may be applied, for example in a system where only one guidewire is used or in a system where two or more (e.g., 3, 4 or more) guide wires are used. In some exemplary embodiments of the invention, a considerable saving in balloon complexity and/or diameter is provided.

Figure 3H:
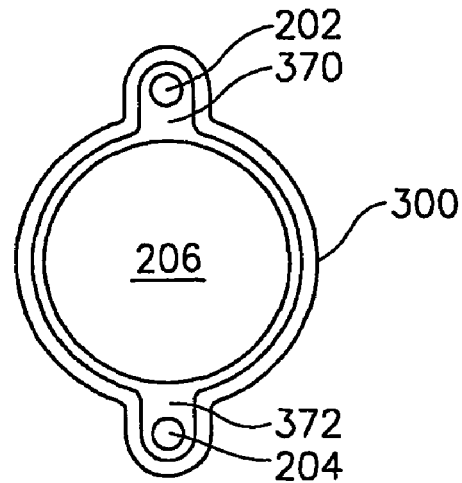
FIGS. 3H-3J illustrate stent guide wire channels for a channel-less balloon catheter, in accordance with exemplary embodiments of the invention.
Figure 3I:
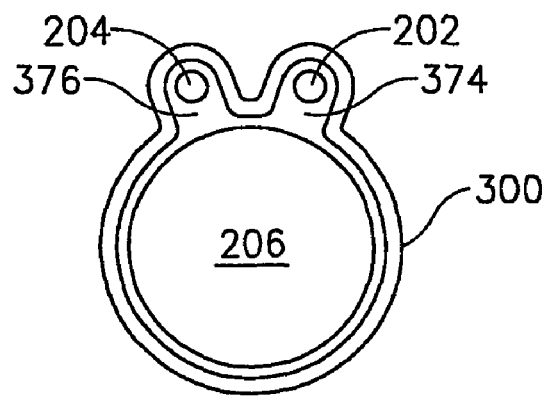
Figure 3J:
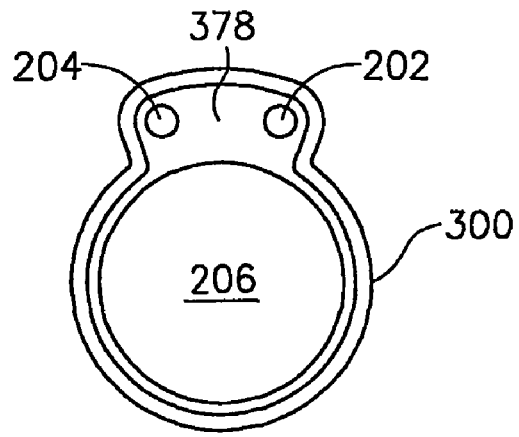

FIGS. 3H-3J illustrate stent guide wire channels for a channel-less balloon catheter, in accordance with exemplary embodiments of the invention.

In FIG. 3H, two guidewires 202 and 204 have separate channels 370 and 372 defined in stent 300. While the channels are shown opposite from each other, they may be at any angle relative to each other.

In FIG. 3I, two channels 374 and 376 are shown side by side.

In FIG. 3J a single shared channel 378 is shown.

It should be appreciated that the relative angular position of the channels may vary along the length of the stent. Alternatively or additionally, the channels may start as shared and/or end as shared and have a non-shared section as well. A channel need not be defined along an entire stent, for example, two axially displaced channels may be defined, for example one for each guide wire or for a single guide wire that is not in any channel between them. Alternatively or additionally, one or both channels may include one or more exit and entry points along the stent and/or not be defined for the entire length of the stent, for example being defined only for a distal or proximal portion of the stent or in its middle.

FIGS. 4A-4F illustrate a crimping method and a corresponding crimped stent in front cross-sectional and side views, in accordance with an exemplary embodiment of the invention.

It should be noted that in some exemplary embodiments of the invention, known stents are crimped using the crimping method, not only stents having the design of stent 300.

FIG. 4A shows a front view and FIG. 4B a side view of uncrimped stent 300.

FIG. 4C shows a first crimping sage device comprising two forms, 402 and 404, of which form 404 has an arcuate cross-section and form 402 has a depression 406 along at least part of its length. The forms may be of any type known in the art. In a particular example, the form are rigid and are pressed together manually. Alternatively, they are pressed by a machine. In another example, the forms are elastic. In another example, more than two forms are used. In another example, the forms collapse using an iris-like mechanism. In another embodiment of the invention, a hand crimping tool for example where forms 402 and 404 are jaws of pliers or a vise, is provided; a separate hand tool may be provided for each stage. Using a hand-tool may allow on-the-spot selection of the channel length for channel 304 and/or greater freedom with selecting stents, balloons and/or delivery systems. FIG. 4D is a side view of stent 300, showing partial formation of channel 304. Inner forms may be provided in this first crimping step as well, if desired.

FIG. 4E shows a second crimping stage, in which balloon 208 is provided for stent 300 to be crimped on and a guidewire form 408 is also provided, to assist in forming channel 304. The two outer forms shown are a plain form 414 and a partially scalloped form 412 with a depression 416 matching channel 304. FIG. 4F is a side view of the crimped stent. In other embodiments of the invention, crimping is done in a single step or in more than two steps.

In an alternative embodiment, guide wire form 408 is provided over the entire length of the stent, exiting though the desired aperture area. A uniform crimping tool, with a non-circular cross-section may be used.

The stent may be made of any suitable bio-compatible or coated material. For example, one or more of the following materials may be used: plastic, biodegradable plastic, Platinum, Ti-15Mo (ASTMF 2066-01), PP1100, a Cobalt-Chromium alloy, Tantalum, a Niobium alloy, 3L6L, MP35N, Titanium, Titanium alloys, such as HOWMEDICA® TMZF® and Titanium-nickel alloys, such as NiTinol. Various ingrowth enhancing or preventing coatings and other treatments, such as radioactivity and drug elution may also be provided using the stent.

In an exemplary embodiment of the invention, the stent is made relatively softer and/or thinner where the bending amount is greater. This is optionally used for one or more of the following reasons. One is to prevent failure of the stent material. Another is to allow the strain to focus on these plastically deformed areas and reduce spring back caused by elastically deforming areas elsewhere in the stent. Another is to allow stronger materials to be used, for example a tantalum niobium alloy, titanium or a titanium molybdenum alloy, such as ASTM F2066, a wrought titanium-15 molybdenum alloy.

In an exemplary embodiment of the invention, the stent is made softer by annealing it locally. Optionally, the stent is made hard, for example by cold working and then annealed where plastic deformation (e.g., with increased elongation ability) is expected (and/or desired). Alternatively or additionally, some parts of the stent are treated, for example chemically to make them harder.

Alternatively or additionally, elastically deforming sections of the stent may be made shorter or thicker (or treated to be stiffer) so that they are less affected by the expansion and, optionally, spring-back is reduced.

While an axial channel 304 is shown, this is not required. For example, the channel can be spiral or bent. One use of such a shaped channel is for aiming the guidewire in a direction that is non-axial. If the spiral has a varying pitch, exiting the guidewire at different points along the channel, will define different such angles. Alternatively or additionally, multiple different stents are provided with different angles and/or exiting positions (e.g., channel lengths). Alternatively or additionally, the channel is not solid, so that guidewire can exit at several points along its length. Possibly, a retractable overtube is provided to prevent exiting of the guidewire from the stent at point prior to the ending of the overtube (which is retractable relative to stent).

User selection of exit point and angle may be possible in other embodiments of the invention, for example, where the channel is formed in the catheter or in the balloon, rather than by the stent. It should be noted that in some embodiments of the invention, the guidewire is mounted on the stent delivery system (or vice versa) outside the body, where such selection is relatively convenient.

While the above description has focused on a plastically deformed stent, it may also be used for shape memory stents (which are plastically deformed for insertion) and super elastic or elastic stents, where an overtube may be provided to prevent early expansion. This overtube may be, for example, apertured or slotted, to allow exit of guidewire 204.

As noted above, other methods may be provided for allowing a guidewire to exit midway along a balloon.

Figures 5A, 5B:
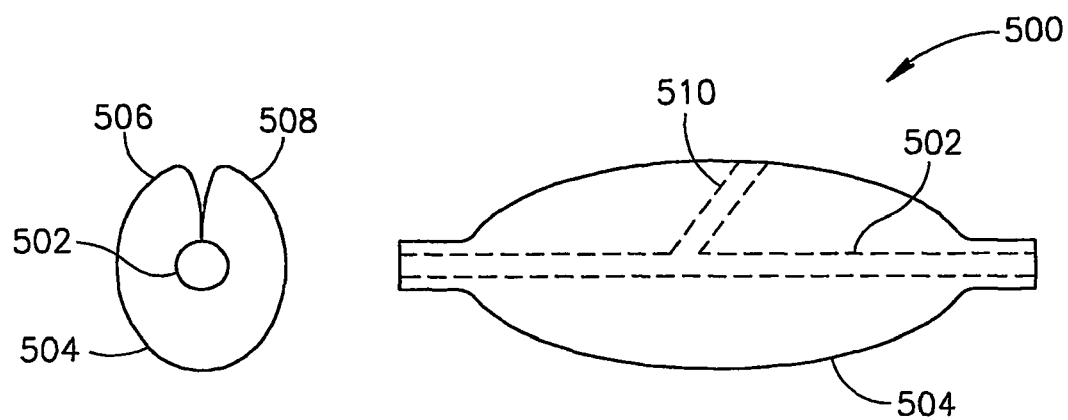
FIGS. 5A and 5B show a balloon with a middle exit for a guidewire, in accordance with an exemplary embodiment of the invention.

FIGS. 5A and 5B show a balloon 500 with a middle exit 510 for a guidewire, in accordance with an exemplary embodiment of the invention. In this embodiment, a balloon 504 comprises two lobes 506 and 508, at least along part of its axial extent. While the lobes are shown on only one side of balloon 504, the entire balloon may be comprised of two lobes (e.g., with the entire balloon split into two side by side balloon). A slit is defined by the lobes and serves as an exit 510. Optionally, the lobes also include recesses that further define exit 510 as a tube, however, this is not required. In an exemplary embodiment of the invention, when the lobes are not inflated, the guidewire can exit, with little resistance. In some embodiments, the lobes need to be partially deflated, to reduce resistance. Optionally, however, some inflation is provided, so that the balloon does not collapse and block exit 510.

A single, branching guidewire channel 502 may be provided, with an aperture for the guidewire to exit. Alternatively, separate guidewire channels are provided for different guidewires.

Figure 6A:
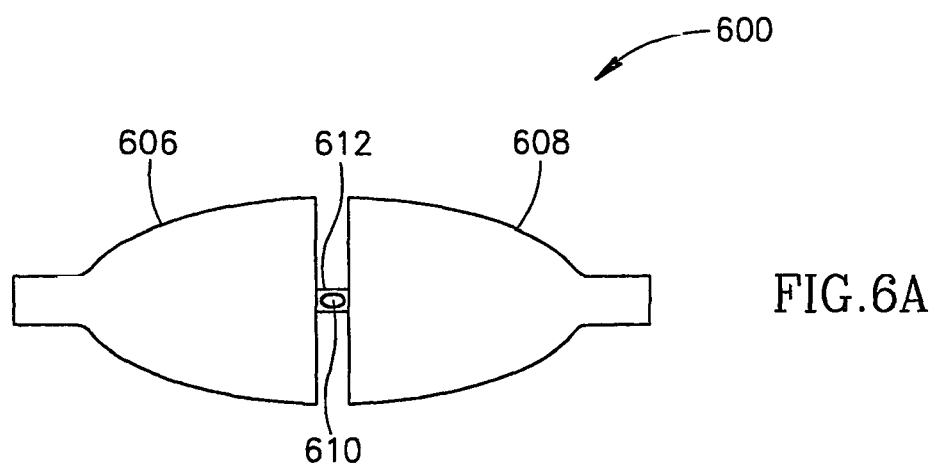
FIGS. 6A and 6B show a balloon with a middle exit for a guidewire in accordance with an alternative exemplary embodiment of the invention.
Figure 6B:
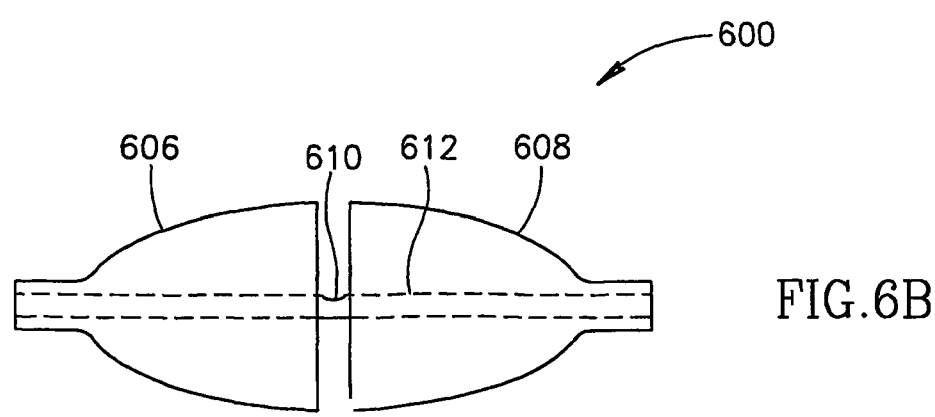

FIGS. 6A and 6B show a balloon 600 with a middle exit for a guidewire in accordance with an alternative exemplary embodiment of the invention. In this embodiment, two axially separate balloon sections 606 and 608 are provided, a guidewire can exit through an aperture 610 in a guidewire channel 612. Optionally, the balloons also define a radial channel for the guidewire. Optionally, the angle between the balloon is not perpendicular to balloon 600, but at an angle.

The two balloons optionally share a single inflation lumen. Optionally, one balloon is softer, so that it inflates first.

Optionally, channel 612 has a thin side facing the exit direction, for example allowing a physician to select an exit point at will, by poking a hole or tearing the thinned or a weakened part of the channel.

Figure 7A:
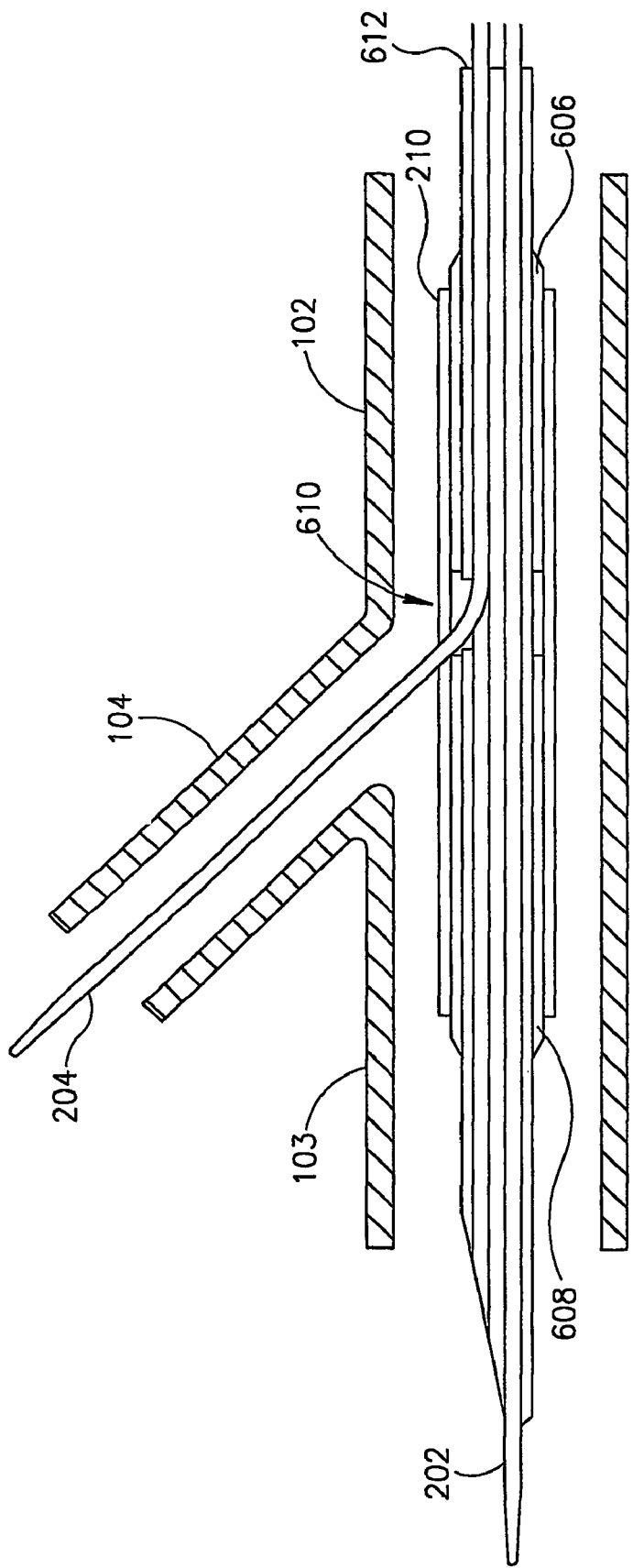
FIGS. 7A and 7B illustrate the use of the balloon of FIG. 6, for treating the bifurcation of FIG. 1, in accordance with an exemplary embodiment of the invention.
Figure 7B:
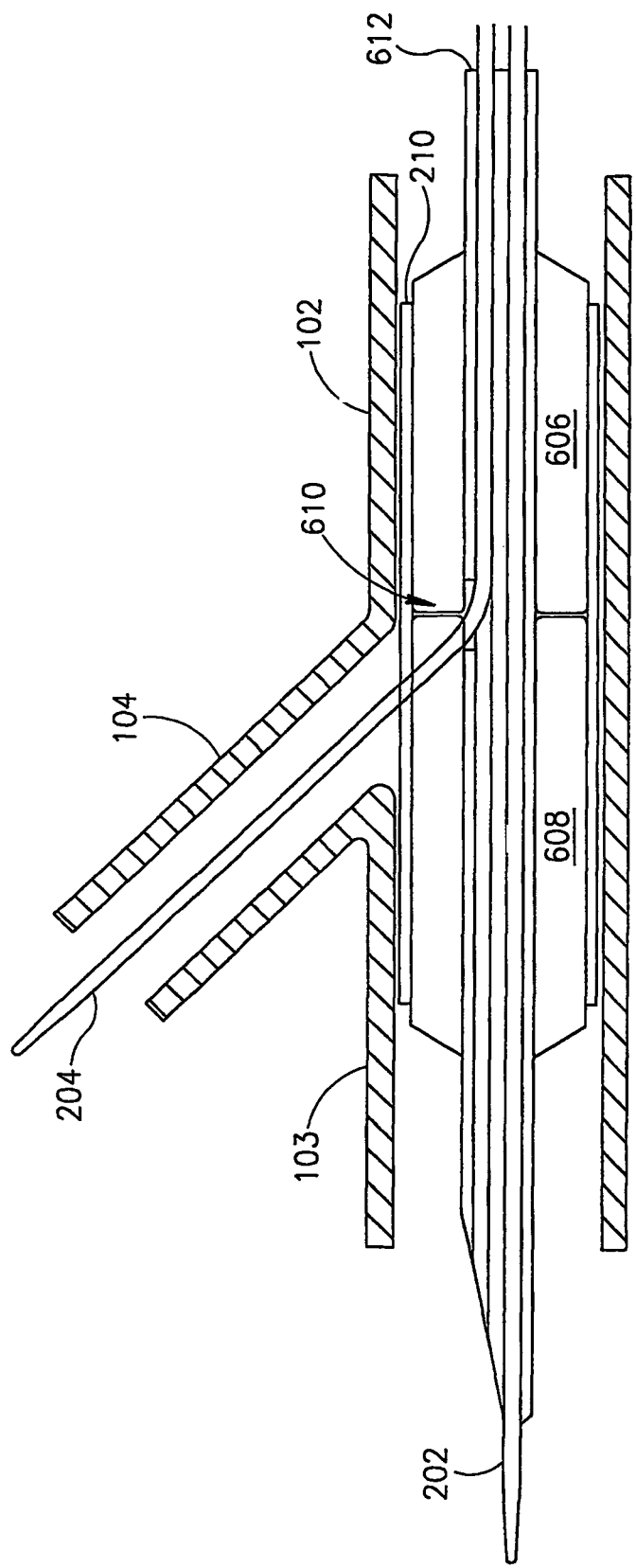

FIGS. 7A-7B illustrate the use of the balloon of FIG. 6, for treating the bifurcation of FIG. 1, in accordance with an exemplary embodiment of the invention. Drawing on what was shown in FIG. 2, FIG. 7A corresponds to FIG. 2B. FIG. 7B corresponds to FIG. 2C. Balloon section 608 is shown in this embodiment to be slightly axially slotted, to define a path for guidewire 204 that is not perpendicular to the balloon axis.

The two guidewires may, for example, share a channel, or as shown, have different channels.

In FIGS. 5-7, the stent can be passive, with regard to aiming guidewire 204 Alternatively, the stent is used for aiming. For example, the guidewire exit direction may be defined by the following two points, aperture 610 and the point on stent 210 where the guidewire exits.

It should be noted that in some embodiments of the invention, once stent 210 is in place, if passage of stent 210 tears balloon 606 or balloon 608, this may not be a problem, for example, if these balloons are already not needed. In such a case, they may be retracted first.

FIGS. 8A-8D illustrate guidewire releasing balloons in accordance with exemplary embodiments of the invention FIG. 8A shows cross-sectional view of a balloon catheter 800 inside a vessel 801. Only a single lumen 802 is shown, for example an inflation lumen or an inner-guidewire channel, however, more lumens many be provided. A balloon 806 is shown closed up. A guidewire 804 is shown trapped within a channel 809 defined by a membrane on the outside of balloon 806. Optionally, a stent 810 is provided on balloon 806, however, such a stent is not always provided, as balloon 806 defines the guidewire channel. In other embodiments, the stent prevents release of guidewire 804, as long as the stent remains mounted on the balloon. In an exemplary embodiment of the invention, the membrane is thickened, stiffened and/or otherwise treated (e.g., by attaching another layer, or by being surface treated) at a section 808 about channel 809. In an exemplary embodiment of the invention, this stiffening assists in preventing unfurling of balloon 806 and premature release of guidewire 804. Alternatively or additionally, this section protects the balloon form the guidewire. Alternatively or additionally, this section provides reduced friction between the balloon and the guidewire.

Alternatively or additionally, guidewire channel 809 is defined between lobes of the balloon, by the pattern of folding of the balloon, when folded onto a guidewire. Some glue is optionally provided to prevent unfurling of balloon 806.

Alternatively or additionally to providing a section 808, channel 809 may be closed, for example by a drop of glue or a thin tearable membrane 812.

FIG. 8B shows the effect of inflating balloon 806. Typically, vessel 801 will be expanded. In addition, channel 809 is opened and the guidewire is released. In one example, section 808 is plastically deformed by the expansion. Alternatively or additionally, the drop of glue or membrane 812 is torn by the inflation. In one embodiment of the invention, the membrane is torn when a tool (e.g., other balloon, stent) is provided over guidewire 804. Alternatively to what is shown, the inflation of balloon 806 may have the profile of a full circle. Optionally, the balloon is designed to release the guidewire when a high enough pressure is applied, for example, that used to inflate a stent, for example 1 atmosphere.

FIG. 8C is a side view of balloon catheter 800 in accordance with one embodiment of the invention, showing that section 808 is defined at a series of points 818, each one having the shape of a "C". This method may be useful to prevent reduction of balloon flexibility.

FIG. 8D is a side view of balloon catheter 800 in accordance with another embodiment of the invention, showing that section 808 is defined as an elongate section 820. This method may be useful to ensure retention of guidewire 204 and/or allow guidewire 204 to be recaptured if section 820 is elastic.

It should be noted that points 818 and section 829 need not travel in a straight line, start at an end of the balloon or end at its middle. For example, these designs (e.g., FIGS. 8A-8D) may be used to allow a balloon catheter to avoid the need for a guidewire lumen or provide a lumen-less balloon, which may be, for example, narrower and/or more flexible. Alternatively, the channel defined by the sections or points may be contiguous with a channel defined in the non-balloon body of catheter 800, for example distal or proximal to balloon 806.

Figure 9A:
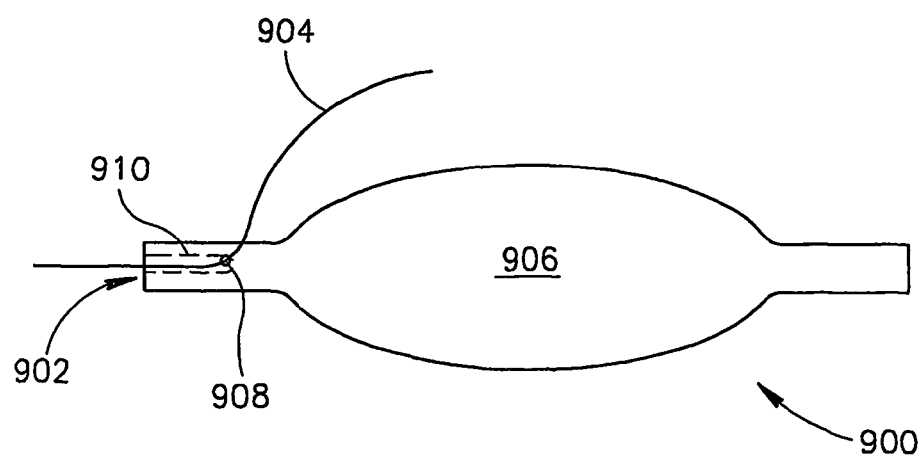
FIGS. 9A and 9B illustrate catheters with tearable guidewire channels, in accordance with exemplary embodiments of the invention.
Figure 9B:
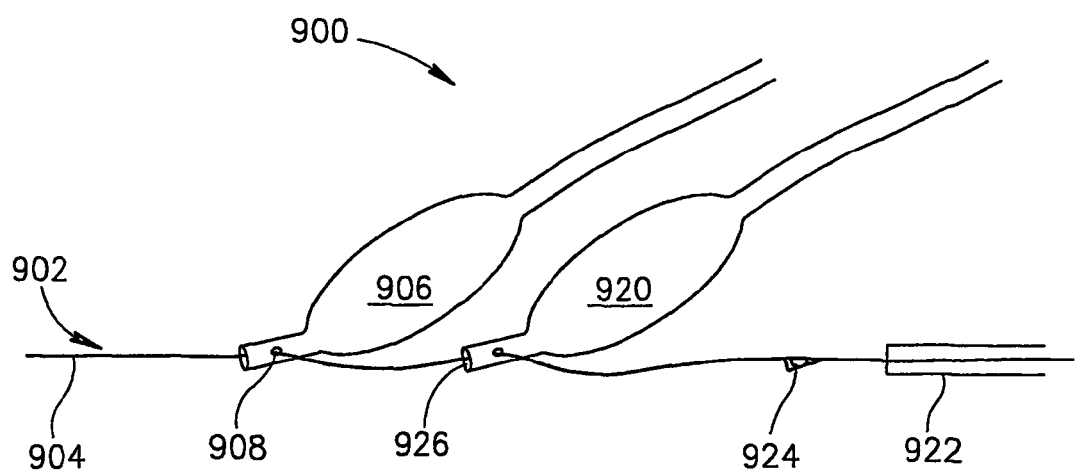

FIGS. 9A and 9B illustrate catheters with tearable guidewire channels, in accordance with exemplary embodiments of the invention. FIG. 9A shows a balloon catheter 900 mounted on a guidewire 904. A channel 902 is defined in a distal portion of the catheter, distal of a balloon section 906. Channel 902 includes a tear section 910, for example, a weakened or thin portion, which is designed to fail first. In an exemplary embodiment of the invention, channel 910 is all distal of balloon 906, with an exit 908 for guidewire 904 also being distal to the balloon. Optionally, the attachment of the membrane of balloon 906 to the distal portion of the catheter body is by inward folding of the balloon membrane, towards the proximal side, rather than by simple welding to the catheter body. In other embodiments of the invention, the channel is defined proximal to the balloon or through the balloon. It should be noted that the balloons of FIG. 8 can also act as tearable balloons, in some embodiments of the invention.

FIG. 9B illustrates various methods of tearing a catheter 900 off of guidewire 904. Such tearing may be useful, for example, if it allows easy removal of catheter 900.

One tearing method uses a tube 922 having a diameter greater than channel 902 and/or opening 908. When tube 922 is advanced or catheter 900 retracted, tube 922 tears open channel 902. Optionally, tube 922 rides guidewire 904 only on a portion adjacent its tip, rather than along its entire length.

Another tearing method is providing a thickening or bump 924 on guidewire 904, with the same function. This bump may be provided on an exchanged guidewire, so that catheter 900 need not have first advanced over the bump. However, careful advancement or advancement in one direction over the bump need not have the same tearing effect as retraction.

Another tearing method is by a leading edge 926 of a next tool in line 920 tearing off the first tool in line (i.e., catheter 900). This method illustrates the ability to rapidly provide a replacement tool at a replacement site, for example, by pre-loading the guidewire with multiple tools and tearing off old ones when not needed. The pre-loaded tools are optionally parked at a location where the vessel thickness allows two tools to pass side by side. Such replacement may be especially useful where the guidewire is long and convoluted, for example in the brain.

Another method, not shown, is that inflation of balloon 906 causes tearing or eversion of a previously slotted channel. In an exemplary embodiment of the invention, part of the balloon membrane extends into the channel, so that it can expand and tear the channel and/or roll it back.

The above description has focused on devices with two guidewires. However, the devices may include multiple additional channels and, for example, three or four or more guidewires. In an exemplary embodiment of the invention, such a complicated device is used where stenting a vessel with two or more nearby branches. One "side exiting" guidewire channel may be provided for each such side branch. Such complex situations may be found, for example in the brain and near the heart (for short lengths of vessel). As noted above, in some cases, even such complicated stents with multiple branches can be deployed using standard balloons, for example first partially inflating the main branch and then inflating each of the side branches in turn before (or during) finalizing of the main branch. In some cases, the opening in the channel is not along the axis of the stent. This may be provided, for example, by crimping the end of the channel and providing an opening adjacent the crimping.

Especially, but not only, in such complicated stenting situations, it is often the case that a side branch is not at the exact middle of the stented area in the main branch. The term middle has been used as a general descriptive term and not to mean the exact middle. Typically, the exit point for the guidewire is expected to often be between 25% and 75% of the length of the stent. However, for some situations, it may be nearer to either end. Methods for selecting the exit point have been described above.

Figure 10A:
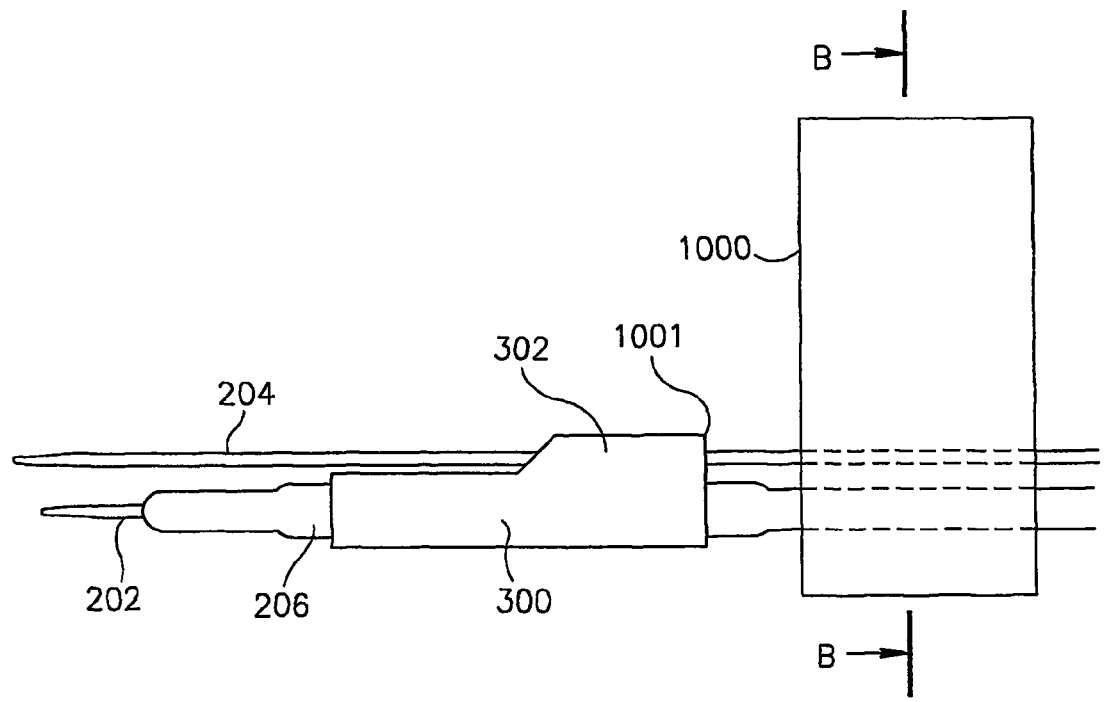
FIGS. 10A and 10B illustrate a guidewire guide for use outside of a body, in accordance with an exemplary embodiment of the invention.
Figure 10B:
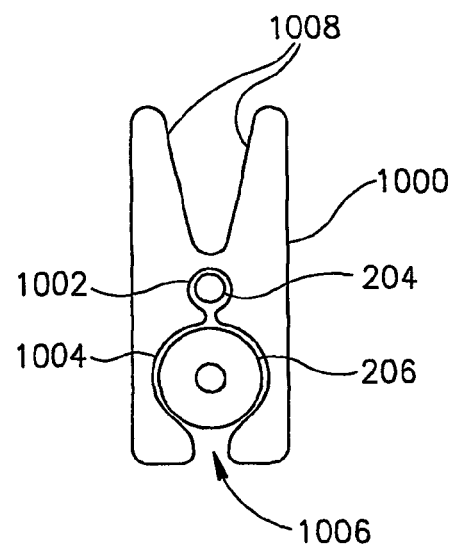

FIGS. 10A and 10B illustrate a guidewire guide 1000 for use outside of a body, in accordance with an exemplary embodiment of the invention. FIG. 10A shows the catheters and guidewires of FIG. 2, with guidewires 202 and 204 already mounted with stent 300 on catheter 206. Guidewire 204 typically extends to the right (e.g., away from the body) a great distance, this may cause inadvertent forces against channel 302 and especially its proximal entry 1001. In an exemplary embodiment of the invention, a guide 1000 is provided which maintains guidewire 204 and catheter 206 in proximity and possibly prevent such force and its potential associated damage. Various designs may be used. FIG. 10B shows a cross-sectional view of a particular implementation in the shape of a cloths pin. A channel 1002 is provided for guidewire 204 and a channel 1004 is provided for catheter 206. Alternatively, a single channel may be shared and/or may have a keyhole shape. In an exemplary embodiment of the invention, when two tabs 1008 of guide 100 are brought together and opening 1006 in an opposite side of the guide widens, so that catheter 206 and/or guidewire 204 may be inserted. Once the catheter and guidewire enter the body, guide 1000 is optionally removed. Optionally, the cannel is smooth and/or lubricated, to prevent damage to the guide wires and/or catheters passed therethrough.

FIGS. 11A-11E illustrate a balloon folding method in accordance with an exemplary embodiment of the invention.

FIG. 11A is a side view of a dual guide-wire balloon 1100, which includes at least two distinct sections, a narrow diameter folded balloon section 1102 and a wider diameter folded section 1104. In an exemplary embodiment of the invention, as shown in FIG. 11B, section 1104 comprises a balloon portion 1112 which is folded in a manner which defines a channel 1120. One method of such folding is shown in FIG. 1B, in which balloon portion 1112 is flattened to form two leaves 1116 and 1118 which are curled to overlap at their tips and define channel 1120. The actual folding process may be performed on a tube and, an exemplary method is described below. FIG. 1B also shows a lumen 1122 defined by a tube 1114. Tube 1114, may be, for example, a guide channel for a guide wire or an inflation lumen for balloon portion 1112.

FIG. 11C is a cross-sectional view of narrow diameter section 1102, in which a balloon 1110 is folded so that its two flaps 1124 and 1126 have a greater overlap and no lumen 1120 is formed. Optionally, the balloon at section 1102 folds over itself using more than two flaps, for example, using three, four or more flaps.

In the embodiment shown, between sections 1104 and 1102, an exit section 1106 is provided, in which an opening 1108 is defined, for exiting of a catheter or guidewire out of channel 1120. Optionally, as shown, the balloon is has a (expanded) narrower diameter at section 1106. Alternatively or additionally, a second fold of the balloon is provided opposite opening 1108 on a diametrically opposite side the channel.

FIG. 11D is a perspective view of section 1106.

While a two lumen balloon is shown, a multi-section balloon, with, for example, two or more exit points and/or three or more lumens, may be provided. Channel 1120 may be sized, for example for a guidewire or for a balloon catheter, or possibly for a stent-carrying catheter. In an exemplary embodiment of the invention, channel 1120 has an inner diameter of between 0.5 and 0.9 mm, for example a 0.9 mm channel for a 4 mm diameter balloon.

FIG. 11E shows balloon 1100 having a guide wire 1132 passed through lumen 1122 and a tube 1130, for example, a balloon catheter, which passes through lumen 1120 and opening 1108.

In an exemplary embodiment of the invention, balloon 1100 is marked with one or more radio-opaque markers, for example bands (not shown). In an exemplary embodiment of the invention, a marker is provided at the part of the balloon corresponding to the bifurcation point, to assist in correctly positioning the stent. It is noted that often the band on the balloon will be easier to see in a moving fluoroscopic image than a single dot on the stent.

Figure 12A:
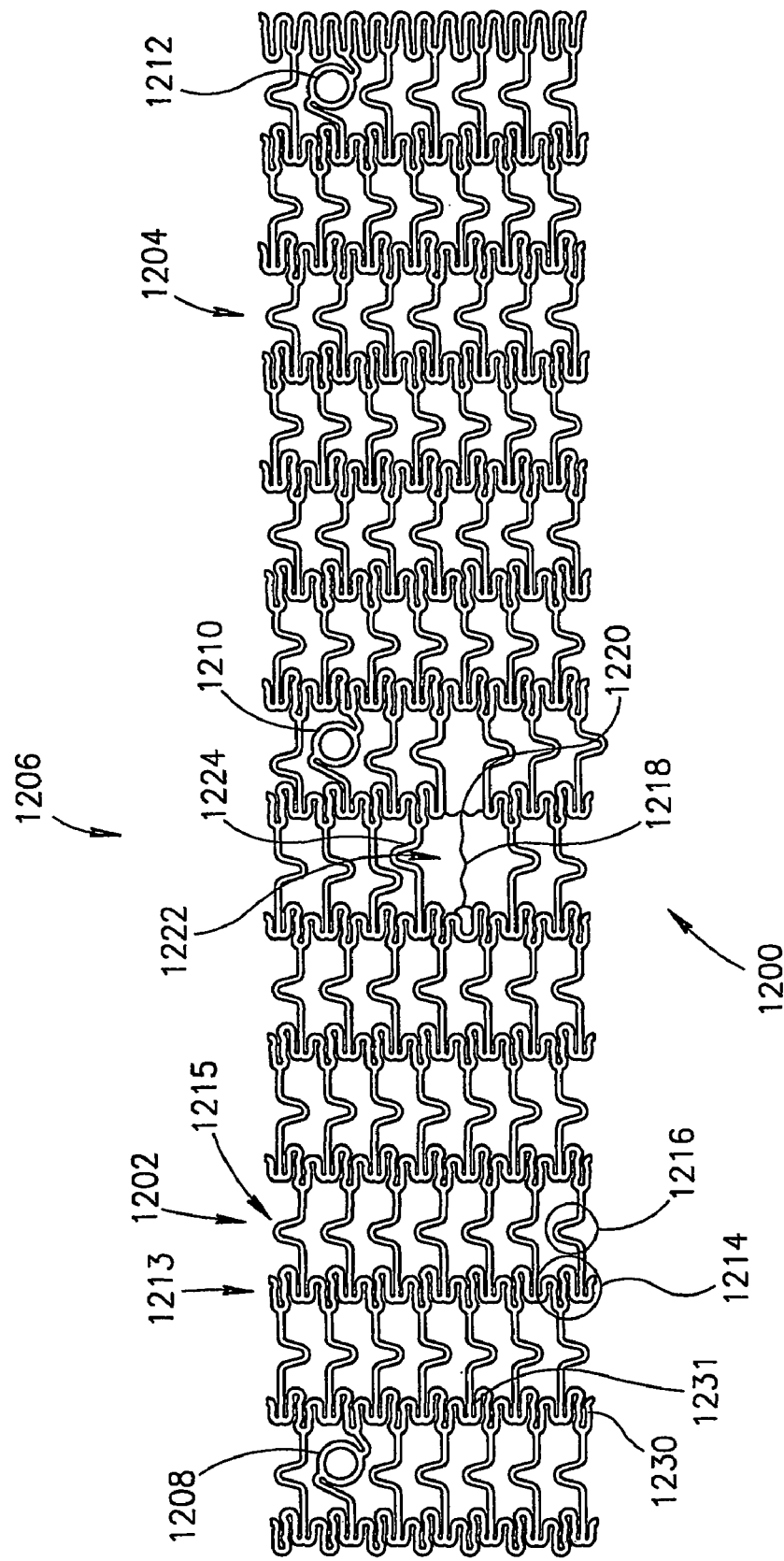
FIGS. 12A-12B illustrate a stent in plan view and mounted on a balloon catheter, in accordance with an exemplary embodiment of the invention.
Figure 12B:
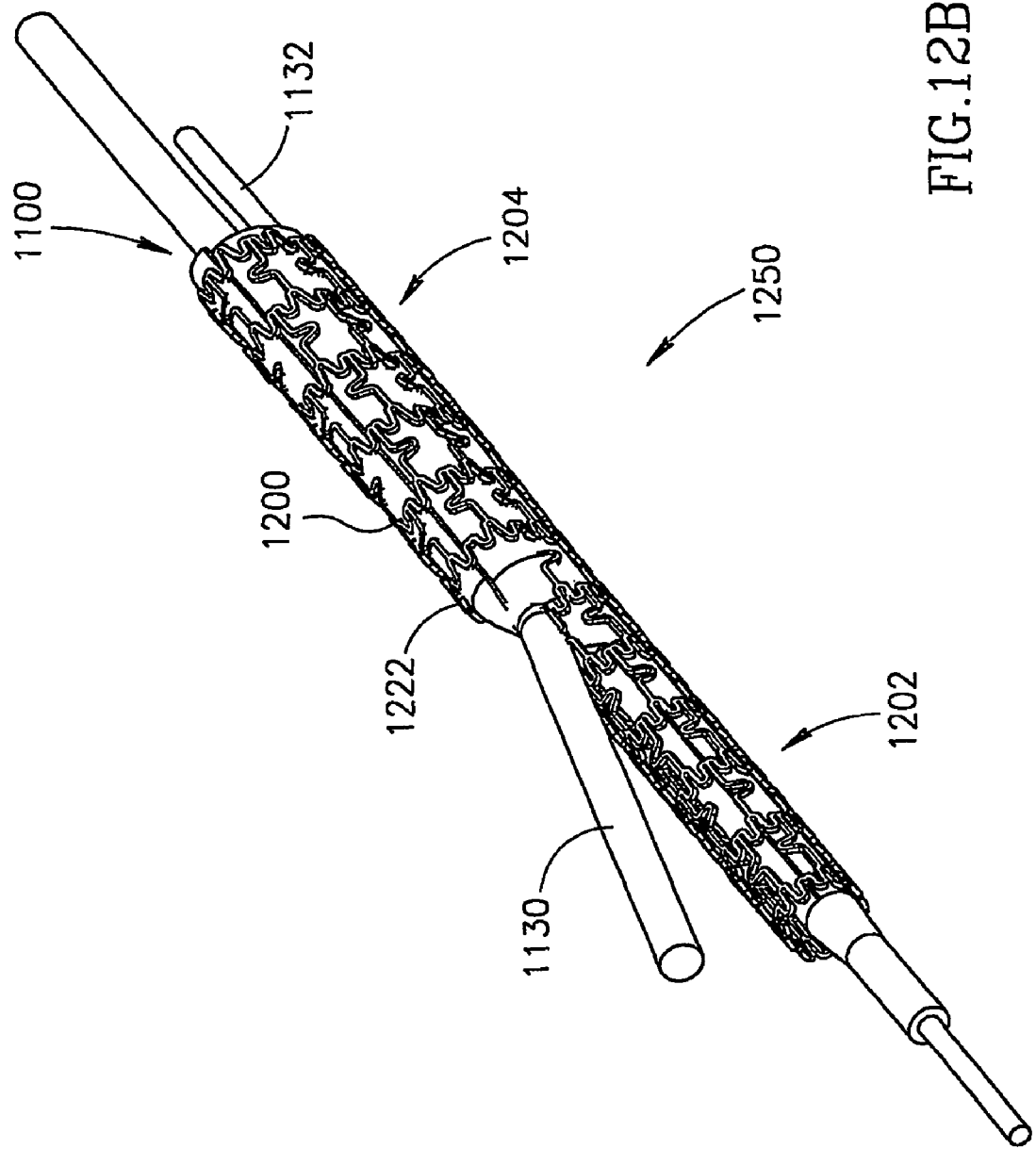

FIGS. 12A-12B illustrate a stent 1200 in plan view and mounted on a balloon catheter, in accordance with an exemplary embodiment of the invention.

Stent 1200 comprises three sections, a narrow section 1202, a section with an aperture, 1206 and a wider section 1204. In some embodiments of the invention, the narrow and wider sections are sized to match vessel diameters before and after bifurcation. Alternatively, sections 1202 and 1204 have the same diameter, however, when expanded they have different final diameters, for example; 15% difference in diameter. Section with aperture 1206 may be oriented towards narrow section 1202 or towards wider section 1204, depending on the direction of stent insertion. Alternatively, there is no preferred direction except that set by the actual mounting of stent 1200.

In the exemplary embodiment of the invention shown, the stent body comprises alternating bands 1213 of convoluted bends 1214 and bands 1215 of links 1216. Optionally, links 1216 have a small degree of axial freedom and radially are only limited by convoluted bends 1214. In the embodiment shown, a minimum curve radius is desired, however, this would prevent the stent from being sufficiently radially collapsible due to clashing of the curves. In an exemplary embodiment of the invention, a convoluted bend structure is used, in which two adjacent bends, e.g., bends 1230 and 1231 are staggered so that there can be a greater curve radius. This structure also allows a laser to be used to cut the inside of the curves, in spite of the laser minimum beam width. A greater expansion of one side of the stent may be provided, for example, by bands 1213 being longer on one side of the stent.

Optionally, one or more radio-opaque markers are provided. For example, as shown, three markers are provided, a narrow section marker 1208, a wide section marker 1212 and an aperture section marker 1210 which is optionally in line (or at a known axial) distance from an aperture 1222 of section 1206. In an exemplary embodiment of the invention, marker 1210 is designed to be aligned (when stent 1200 is properly placed) with a prominent radiological feature, for example, a wall of the side vessel, or midway between the walls. The markers may be, for example, laser welded or attached by any other means and may be formed, for example of Gold, Titanium or Tantalum. Other suitable materials, possibly for non-x-ray imaging, may be used as well. Stent 1200 may be coated with various materials as known in the art, for example, anti-inflammatory, growth enhancer, growth inhibitor and/or antibiotic materials. As noted above, the balloon may be marked with radio opaque markers, for example bands, instead of or in addition to the stent and especially at the middle area of the balloon corresponding to the location of the side vessel.

In an exemplary embodiment of the invention, aperture 1222 is formed by removing one axial link 1218 and one radial convoluted bend section 1220. As shown, aperture 1222 is narrower in the direction of wide section 1212. In an exemplary embodiment of the invention, it is desired to prevent entanglement of a guide wire with stent 1200 adjacent aperture 1222. In an exemplary embodiment of the invention, the bends in the links are turned away from the aperture, for example, an axial link 1224 is turned away from the aperture.

Referring back to FIG. 2B, the guidewire in the side channel may open the folded flaps of the balloon. The narrowing in aperture 1222 may assist in preventing this, however, this is not essential in some embodiments. Optionally, at least some of the links near the narrow side of aperture the links are make weak enough so that they can be pushed aside by the advancing balloon catheter. Alternatively or additionally, prior to balloon 110 reaching the bifurcation area, and which the two guidewires are not at a large angle relative to each other, the side-balloon is advance a small amount past aperture 1222. It is expected that in some designs, due to the small angle, the balloon will exit through the larger part of aperture 1222 and/or it will be easier for it to widen the narrow section of aperture 1222.

FIG. 12B schematically shows stent 1220 mounted on balloon 1100 such as folded in FIG. 11E, giving a mounted stent system 1250.

In an exemplary embodiment of the invention, the following process is used for folding and/or mounting the stent for FIGS. 11-12.

(a) The balloon (1110 and 1112, as a single segment) is mounted on tube 1114 and slightly inflated.

(b) The balloon is then held against the tube along its middle on two opposite sides of the tube, for example by hand or machine.

(c) Vacuum is applied to the balloon causing it to deflate. Optionally, instead of holding the balloon against the tube, the balloon is pinched. In either case, the result is a flat balloon. The two flaps may be at 180 degrees to each other, alternatively, an angle over (or under) 180 degrees (on the side of the channel) maybe useful, for example, under 170 or 160 or over 200 degrees.

(d) The flaps are folded over (e.g., like in FIG. 11C).

(e) Optionally, the balloon is inserted inside an outer sheath a few tines, to smooth its shape.

(f) A stylet, such as a guidewire or thin tube is inserted between the folds and the balloon over the entire length of the balloon. This thin tube may have a smaller diameter than the final channel diameter, as noted below. Alternatively, the balloon may be folded over the stylet. In this case, for example, the stylet need not extend the entire length of the balloon.

(g) An outer sheath is optionally provided over the (soon to be) wider section of the balloon. The wider section may be visually identified, for example, by a radio-opaque band or by a change in the balloon.

(h) The stylet is folded back in the shape of a "U", so that it exits between the folds of the narrow section of the balloon. Alternatively, the stylet has a bent end and is pulled back (i) The folds on the narrow section of the balloon are refolded and optionally re-smoothed. It is noted that if two axially kissing balloons are used, each balloon can be folded a different way. Further, even if not, the refolding of the narrow section or even its original folding can be different than that of the wide section, with an area of in-continuity (between the flaps) formed at the exit section 1106.

(j) Optionally, a thin tube, for example of shrink-wrap tubing, is provided over each section of the folded balloon.

(k) The stent is provided on the balloon. Optionally the stent is manufactured from a tube with a narrower diameter than the folded balloon and is expanded so that it fits over the balloon.

(l) The stent is crimped on at least the narrow section of the balloon.

(m) Optionally, the thin tube is replaced by a tube with a greater diameter, for example, by inserting a conical tube instead of the thin tube. This causes the stent to expand on the wider section and an optional outer form may be provided to control this distortion.

(n) The shrink-wrap tubing is removed.

(o) Optionally, the stent is heated or supplied with an adhesive to encourage it to stick to the balloon.

While the guidewire channel has been shown only about the balloon, the actual channel in the catheter may be of various types, for example, along the entire catheter, only at the balloon, only near the balloon and/or at several points along the catheter.

While the above description has focused on catheters, it also applies to replaceable tools, for example balloons that can be provided along a catheter. However, the potential diameter savings in a catheter may be a reason to apply it to catheters in particular.

It will be appreciated that the above described methods and mechanisms for providing guidewire channels may be varied in many ways, including, for example, the exact materials used for the devices, the direction of bending, method of crimping, stent used, and/or locations of exists for a defined channel. Further, in the mechanical embodiments, the location of various elements may be switched, without exceeding the spirit of the disclosure, for example, switching the moving elements for non-moving elements where relative motion is required. In addition, a multiplicity of various features, both of methods and of devices have been described. It should be appreciated that different features may be combined in different ways. In particular, not all the features shown above in a particular embodiment are necessary in every similar exemplary embodiment of the invention. Further, combinations of the above features, from different described embodiments are also considered to be within the scope of some exemplary embodiments of the invention. In addition, some of the features of the invention described herein may be adapted for use with prior art devices, in accordance with other exemplary embodiments of the invention. The particular geometric forms used to illustrate the invention should not be considered as necessarily limiting the invention in its broadest aspect to only those forms, for example, where a circular lumen is shown, in other embodiments an oval lumen may be used.

Also within the scope of the invention are surgical kits which include sets of medical devices suitable for making a single or several stent applications. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A balloon catheter, comprising:
an elongate body adapted for insertion into a blood vessel;
a balloon attached to a distal end of said body; said balloon having a proximal end and a distal end, and including a longitudinal fold on its outer surface;
a guide-channel adapted to carry at least a guide-wire located within said fold; and,
a first port in said guide-channel for said guide wire at one end of said balloon; and
a second port in said guide-channel for said guide wire located intermediate the proximal and distal ends of said balloon.

2. A catheter according to claim 1, wherein said entry port is proximal to said tool.

3. A catheter according to claim 1, wherein said guide-channel is adapted to carry a second catheter.

4. A catheter according to claim 3, wherein said second catheter is a balloon catheter.

5. A catheter according to claim 1, comprising a second guide-channel adapted to carry a second guide wire.

6. A catheter according to claim 5, wherein said two guide-channels share a common lumen section.

7. A catheter according to claim 6, wherein said second guide-channel defines an aperture in its side for said distal exit.

8. A catheter according to claim 1, wherein said balloon includes a stiffening which defines said guide-channel.

9. A catheter according to claim 1, wherein said balloon includes adhesive which adheres two parts of said balloon to define said guide-channel.

10. A catheter according to claim 1, wherein said balloon is split to define said channel between two sections of said balloon.

11. A catheter according to claim 10, wherein said balloon is axially split.

12. A catheter according to claim 10, wherein said balloon is trans-axially split.

13. A catheter according to claim 1, further comprising a stent.

14. A catheter according to claim 13, wherein said stent is mounted on said balloon.

15. A catheter according to claim 14, wherein said guide-channel is defined between said stent and said balloon.

16. A catheter according to claim 13, wherein said guide-channel is defined by a crimping of said stent.

17. A catheter according to claim 13, wherein said stent includes a dedicated aperture along its length for said exit port.

18. A catheter according to claim 13, wherein said stent defines two guide-channels.

19. A catheter according to claim 18, wherein said stent includes a dedicated aperture along its length for said exit port.

20. A catheter according to claim 1, wherein said guide-channel is wide enough to accommodate a second balloon catheter.

21. A catheter according to claim 1, wherein said entry port is at the proximal end of said balloon.

22. A catheter according to claim 1, wherein an entry port for said guide wire into said guide channel is at a distal end of said balloon.

23. A catheter according to claim 1, wherein an entry port for said guide wire into said guide channel is located at the proximal end of said balloon.

24. A catheter according to claim 1, wherein an entry port for said guide wire into said guide channel is located at the distal end of said balloon, and an exit port for said guide wire from said guide channel is located intermediate the proximal and distal ends of said balloon.

25. A catheter according to claim 1, wherein an entry port for said guide wire into said guide channel is located intermediate the proximal and distal ends of said balloon, and an exit port for said guide wire from said guide channel is located at the proximal or the distal end of said balloon.

26. A catheter according to claim 1, wherein second port is located approximately equidistant the proximal and distal ends of said balloon.

27. A catheter according to claim 1, further including a second guide wire.

28. A catheter according to claim 27 wherein said second guide wire is located in said guide-channel.

29. A catheter according to claim 27 wherein said second guide wire exits said guide-channel through said second port.

30. A catheter according to claim 1 wherein said second port is oriented so that said guide wire passes therethrough in a non-axial direction.

* * * * *